United States Patent
Evans et al.

(10) Patent No.: US 12,167,847 B2
(45) Date of Patent: Dec. 17, 2024

(54) DEVICES, SYSTEMS, AND METHODS FOR COUPLING FLEXIBLE FILAMENT TO SOFT TISSUE

(71) Applicant: CONEXTIONS, INC., Salt Lake City, UT (US)

(72) Inventors: Zackery K. Evans, Woods Cross, UT (US); Roy M. Taylor, Salt Lake City, UT (US); Cody L Gehrke, South Jordan, UT (US); Matthew J. Swift, Cottonwood Heights, UT (US); Erik N. Kubiak, Las Vegas, NV (US)

(73) Assignee: CONEXTIONS, INC., Salt Lake City, UT (US)

(*) Notice: Subject to any disclaimer, the term of this patent is extended or adjusted under 35 U.S.C. 154(b) by 465 days.

(21) Appl. No.: 17/218,504

(22) Filed: Mar. 31, 2021

(65) Prior Publication Data

US 2022/0015759 A1 Jan. 20, 2022

Related U.S. Application Data

(60) Provisional application No. 63/003,277, filed on Mar. 31, 2020.

(51) Int. Cl.
*A61B 17/06* (2006.01)
*A61B 17/04* (2006.01)

(52) U.S. Cl.
CPC ...... *A61B 17/06066* (2013.01); *A61B 2017/0496* (2013.01); *A61B 2017/06104* (2013.01)

(58) Field of Classification Search
CPC ...... A61B 17/06066; A61B 2017/0496; A61B 2017/06104; A61B 17/1146; A61B 2017/0412; A61B 17/0482; A61B 17/0625; A61B 17/0491; A61B 2017/0403; A61B 2017/0472; A61B 2017/06009; A61B 2017/06042; A61B 2017/0608; A61B 17/0469; A61B 2017/1132

See application file for complete search history.

(56) References Cited

U.S. PATENT DOCUMENTS

| | | | |
|---|---|---|---|
| 5,439,467 A | 8/1995 | Benderev et al. | |
| 8,403,947 B2 | 3/2013 | Ochiai | |
| 8,663,253 B2 | 3/2014 | Saliman | |
| 8,801,727 B2 | 8/2014 | Chan et al. | |
| 8,882,834 B2 | 11/2014 | Sinnott et al. | |
| 8,888,849 B2 | 11/2014 | Fallin et al. | |
| 9,314,234 B2 | 4/2016 | Hirotsuka et al. | |
| 9,357,997 B2 | 6/2016 | Sinnott et al. | |
| 9,629,708 B2 | 4/2017 | Sinnott et al. | |
| 9,636,103 B2 * | 5/2017 | Penna | A61B 17/0469 |
| 9,662,105 B2 | 5/2017 | Sinnott et al. | |

(Continued)

*Primary Examiner* — Richard G Louis
*Assistant Examiner* — David P Stein
(74) *Attorney, Agent, or Firm* — David L. Stott

(57) ABSTRACT

Devices, systems and/or methods for fixating soft tissue at a soft tissue site are provided. The system includes a base member with multiple passer devices that carry a first suture therewith. The passer devices and first suture are passed through soft tissue to form loops adjacent at least a portion of the passer devices along one side of the soft tissue. A second suture is threaded through each of the loops and the passer devices are removed from the soft tissue. In this manner, first and second sutures may be coupled to the soft tissue.

14 Claims, 16 Drawing Sheets

(56) References Cited

U.S. PATENT DOCUMENTS

| | | |
|---|---|---|
| 9,675,341 B2 | 6/2017 | D'Agostino et al. |
| 9,955,963 B2 | 5/2018 | Fallin et al. |
| 9,993,332 B2 | 6/2018 | Woodruff et al. |
| 9,999,422 B2 | 6/2018 | Rush et al. |
| 10,335,138 B2 | 7/2019 | Sinnott et al. |
| 10,368,859 B2 | 8/2019 | Sinnott et al. |
| 10,383,720 B2 | 8/2019 | Gustafson |
| 10,390,821 B2 | 8/2019 | Frank |
| 2003/0065336 A1* | 4/2003 | Xiao ................ A61B 17/0469 606/144 |
| 2003/0078599 A1 | 4/2003 | O'Quinn et al. |
| 2011/0028998 A1 | 2/2011 | Adams et al. |
| 2011/0066165 A1 | 3/2011 | Skinlo et al. |
| 2011/0301620 A1* | 12/2011 | Di Betta .......... A61B 17/06066 606/144 |
| 2014/0180313 A1 | 6/2014 | Harrison et al. |
| 2018/0235595 A1* | 8/2018 | Palese ................ A61B 17/0401 |

* cited by examiner

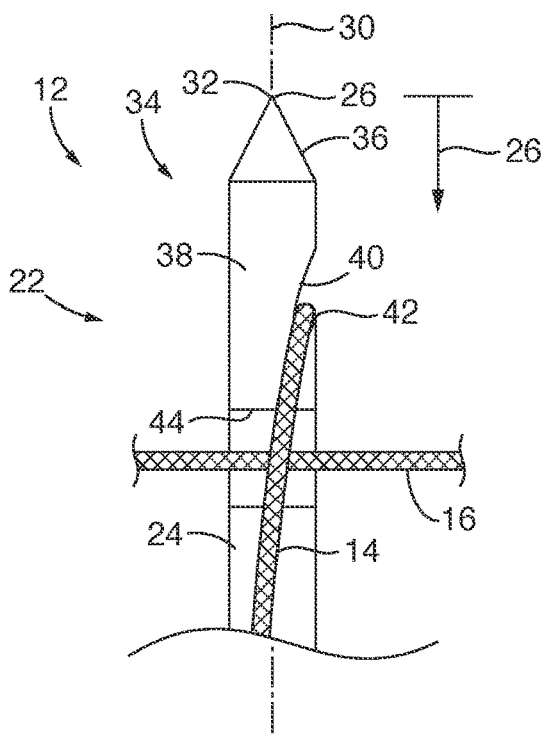
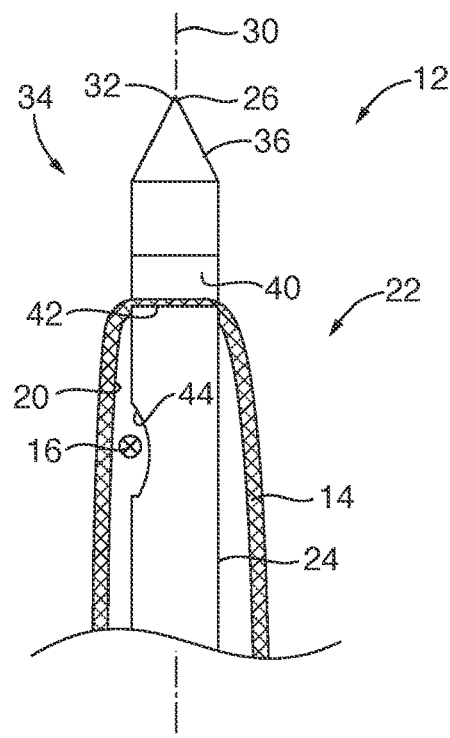
FIG. 1
FIG. 2
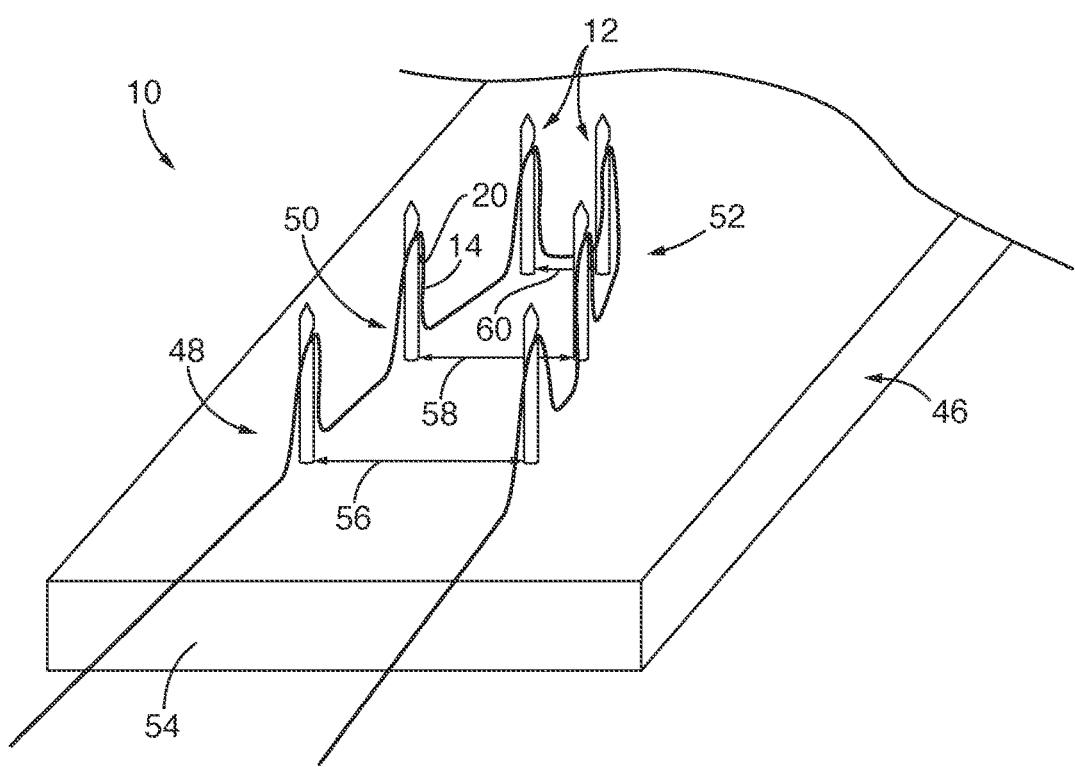
FIG. 3

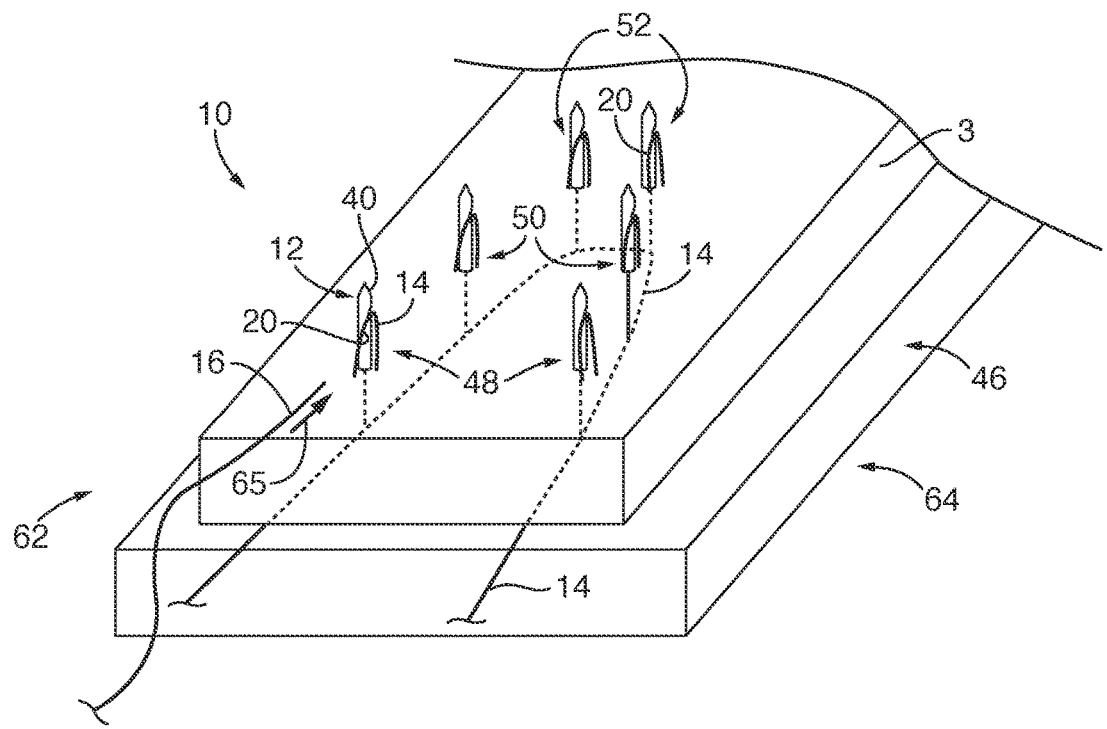
FIG. 4
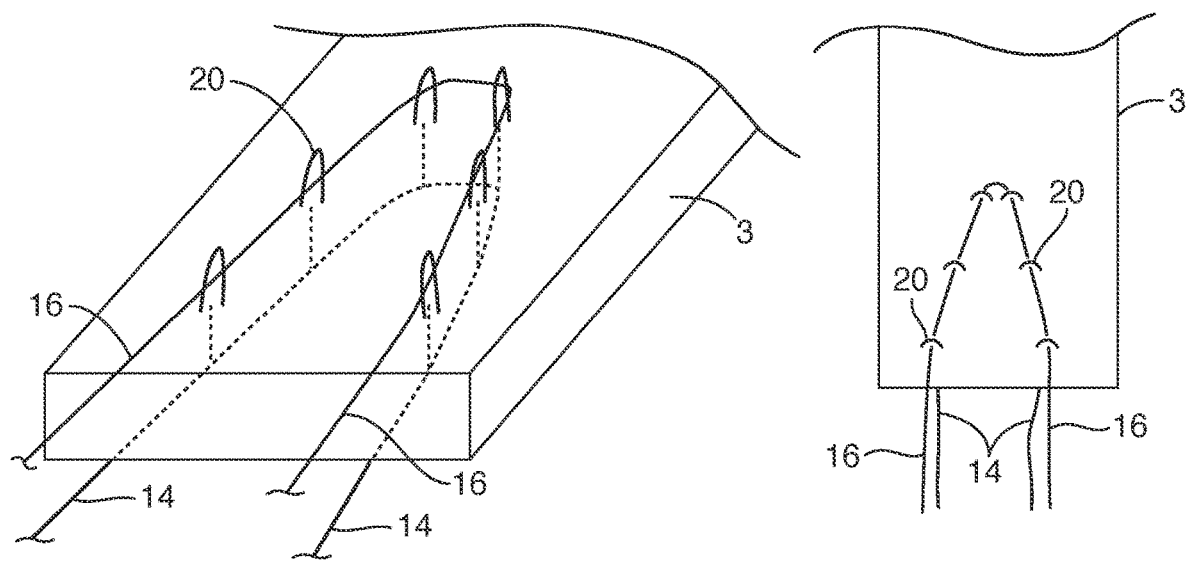
FIG. 5
FIG. 6

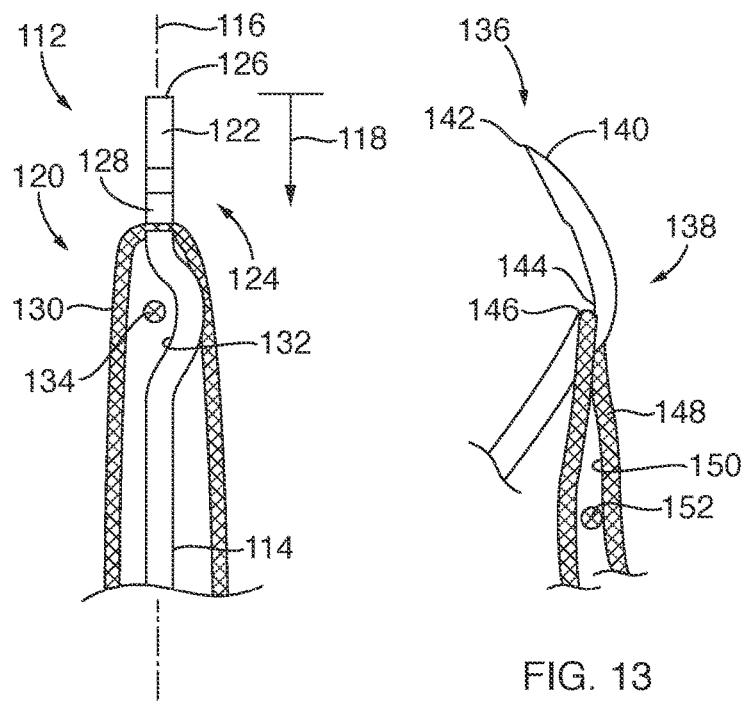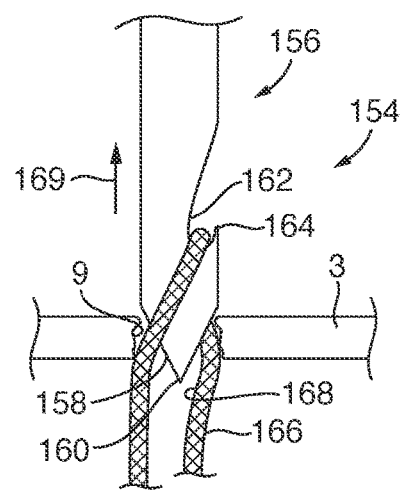
FIG. 12　　FIG. 13　　FIG. 14
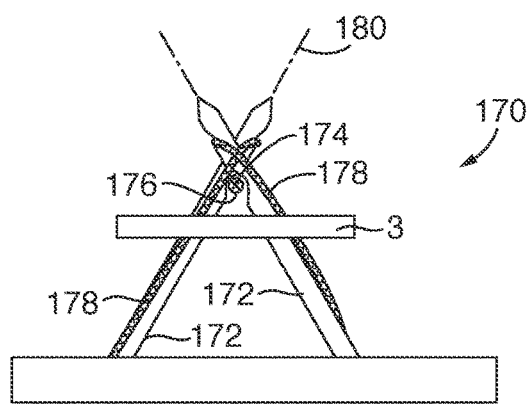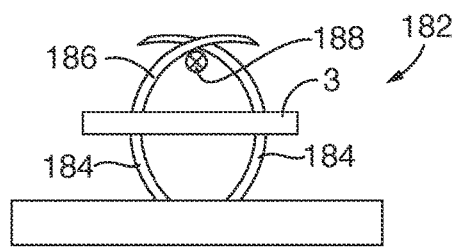
FIG. 15　　FIG. 16

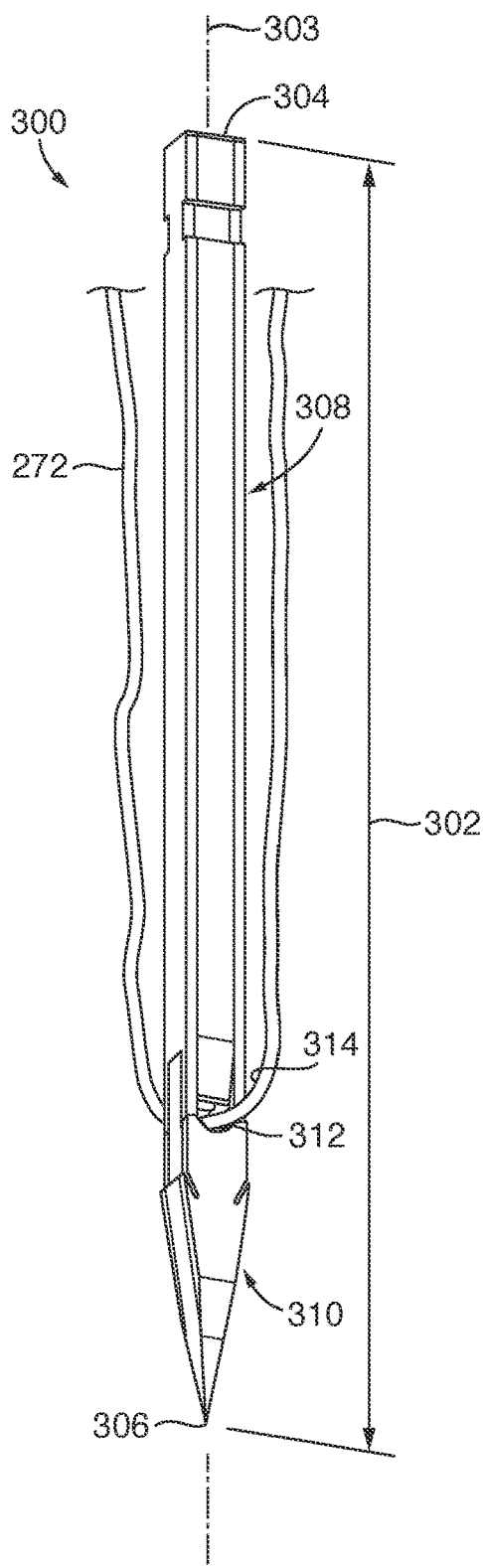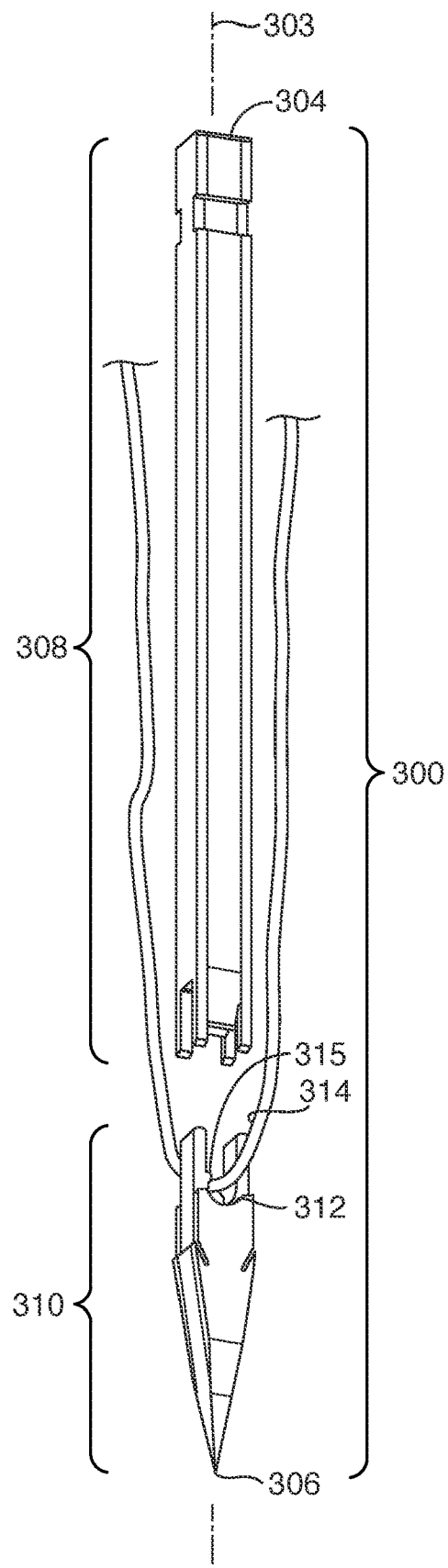
FIG. 28A
FIG. 28B

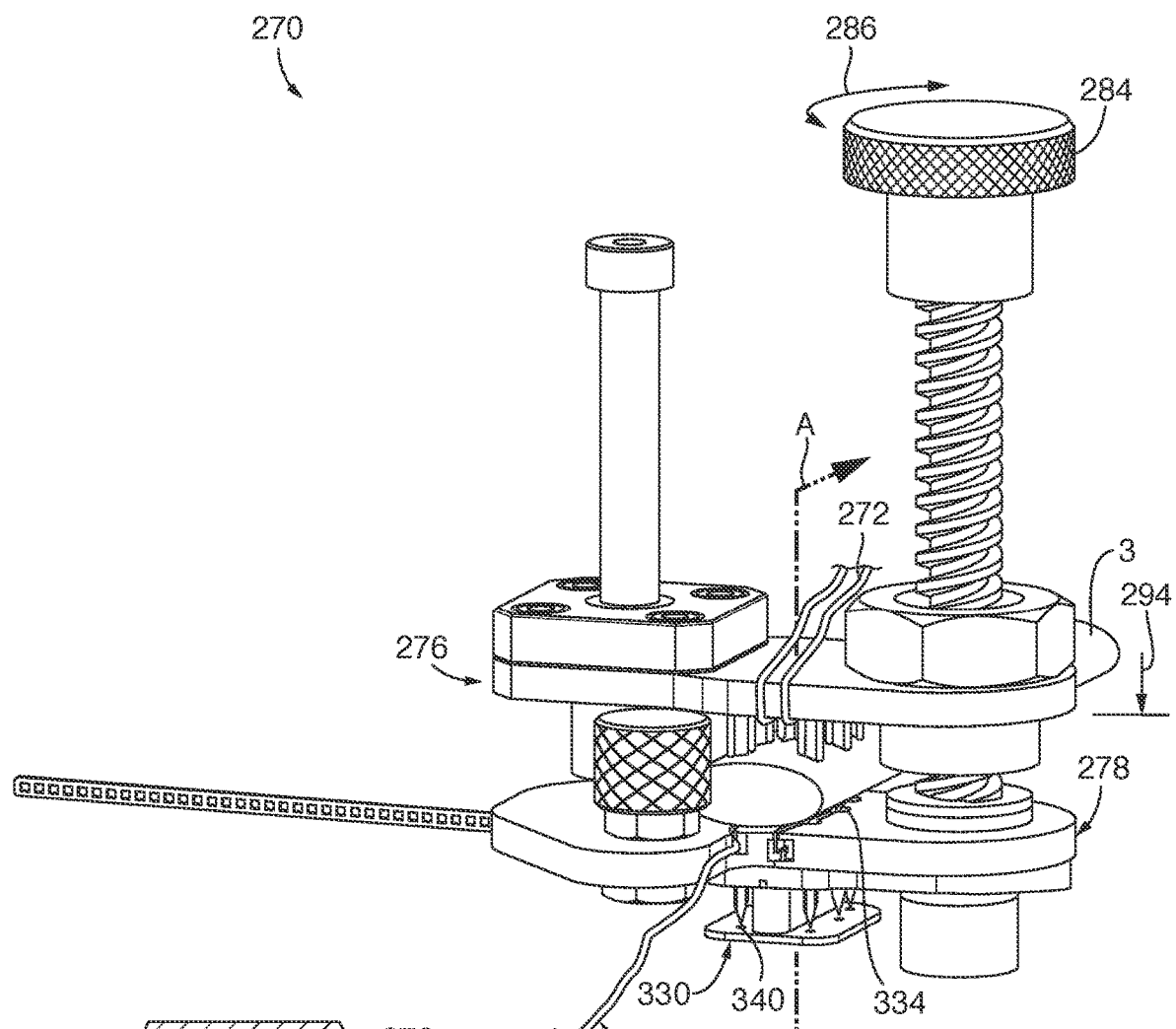
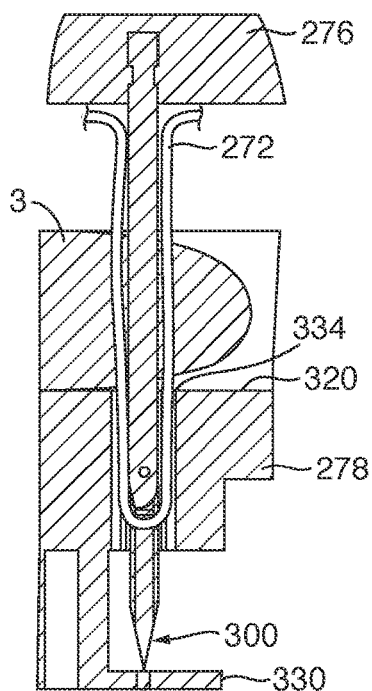
FIG. 30
FIG. 30A

DEVICES, SYSTEMS, AND METHODS FOR COUPLING FLEXIBLE FILAMENT TO SOFT TISSUE

CROSS-REFERENCE TO RELATED APPLICATIONS

The present application claims the benefit of U.S. Provisional Application No. 63/003,277, filed on Mar. 31, 2020, the disclosure of which is hereby incorporated by reference herein in its entirety.

TECHNICAL FIELD

The present invention relates generally to soft tissue repair sites. More particularly, the present invention relates to devices, systems, and methods for repairing soft tissue and attaching soft tissue to bone.

BACKGROUND

Medical practitioners frequently use sutures to repair tissue and facilitate healing. Sutures can be used to close various openings (e.g., ruptures, cuts, punctures, and incisions). They may also be used to fixate soft tissue together, such as tendon and ligament, as well as tendon to bone. Because of their importance and frequent use, several types of sutures and devices for their implantation and extraction have been developed. Typically, fixating soft tissue to bone is implemented with a bone anchor and suture material with suture coupled between the soft tissue and the bone anchor such that the soft tissue is cinched in against the bone. Using suture for fixating soft tissue to soft tissue or fixating soft tissue to bone in an effective manner for appropriate healing requires surgeons with a very high level of skill and experience. However, the best surgeons are not always available when there is a need for appropriate tissue fixation with sutures. As such, it would be advantageous to implement a device or method that facilitates suture fixation to soft tissue that is safe, effective, and provides consistent and repeatable results even for new surgeons or surgeons in training.

BRIEF SUMMARY OF THE INVENTION

Embodiments of the present invention are directed to various devices, systems and methods for fixating soft tissue at a soft tissue repair site. For example, in one embodiment, a passer device system for fixating soft tissue to soft tissue or soft tissue to bone is provided. The passer device system includes a base member, multiple passer devices, a first suture and a second suture. The multiple passer devices extend from the base member, each of the passer devices extending with a length to a tip end and each of the passer devices defining a recess formed along the length thereof. Further, each of the passer devices are spaced from each other in a predetermined configuration. The first suture is sized and configured to extend along the recess of each of the passer devices such that, upon the multiple passer devices moving through the soft tissue, each of the passer devices moves the first suture through corresponding holes formed by the passer devices so that multiple loops are formed by the first suture along each corresponding passer device. The second suture is sized and configured to be threaded through each of the loops and, upon the second suture being positioned within each of the loops, the passer devices are moveable from the soft tissue.

In another embodiment, the recess may be a notch formed in the length of each one of the passer devices. In another embodiment, the recess extends with a hook structure, the hook structure sized and configured to temporally maintain the first suture in the recess.

In another embodiment, the first suture extends with a continuous loop. In another embodiment, the first suture extends between first and second ends. In still another embodiment, wherein, upon the passer devices being withdrawn from the soft tissue, the first and second sutures are moveable to a taut position so as to be coupled to the soft tissue. In yet another embodiment, the wherein, upon the passer devices being withdrawn from the soft tissue, ends of at least one of the first and second sutures are configured to be coupled to a bone anchor. In another embodiment, the passer devices include a second recess defined along a length of each of the passer devices, the second recess sized and configured to facilitate passing the second suture along the second recess.

In another embodiment, the passer device system further includes a second base member with slots defined therein, each of the slots sized and configured to receive one of the passer devices. In a further embodiment, the second base member defines a channel therein, the channel communicating with some of the slots and sized and configured to receive the second suture therethrough. In still another embodiment, each of the passer devices include a tip portion and a body, the tip portion being removably coupled to the body, the tip portion including arms that are moveable to an expanded position.

In accordance with another embodiment of the present invention, a method of fixating soft tissue at a soft tissue repair site is provided. The method includes the steps of: inserting multiple passer devices into soft tissue such that each of the passer devices hold a first suture along a recess defined along an elongated structure of the passer devices; forming loops with the first suture and the passer devices such that the loops extend alongside each one of the passer devices and on one side of the soft tissue; moving a second suture through each of the loops; withdrawing each of the passer devices from the soft tissue; pulling a portion of the first suture to minimize a size of the loops so that the loops move adjacent the soft tissue on the one side of the soft tissue; and pulling ends of the second suture to a taut position.

In another embodiment, the inserting step includes simultaneously inserting at least four passer devices into the soft tissue. In another embodiment, the withdrawing step includes simultaneously withdrawing each of the passer devices. In another embodiment, the withdrawing step includes moving the passer devices from the loops of the first suture. In another embodiment, the withdrawing step includes moving the first suture from the recess of each of the passer devices.

In another embodiment, the inserting step includes pushing the first suture through the soft tissue with the passer devices to form the loops on the one side of the soft tissue. In a further embodiment, the method further includes, subsequent to the inserting step, pulling the first suture through the soft tissue with the passer devices.

In another embodiment, the moving step includes feeding the second suture through a channel defined in a base member. In still another embodiment, the withdrawing step includes leaving a tip portion of each of the passer devices within a base member. In another embodiment, the forming step includes forming the loops with self-expanding arms of each of the passer devices.

In accordance with another embodiment of the present invention, a passer device system for fixating soft tissue at a soft tissue repair site is provided. The passer device system includes a needle base and a threading base. The needle base includes multiple needle passer devices fixed to and extending from the needle base, the needle passer devices including a first suture extending along a portion of a length of each of the needle passer devices so as to extend to define a loop portion associated with each of the needle passer devices. The threading base is coupled to the needle base, the needle base linearly moveable relative to the threading base to change a distance between the threading base and the needle base. The threading base includes a first surface and a peripheral surface, the peripheral surface extending to define a slot entrance opening and a slot exit opening so as to define a guide slot extending through the threading base and extending between the slot entrance opening and the slot exit opening. The peripheral surface defines a threader guide channel that extends between the peripheral surface and the guide slot. The first surface of the threading base faces the needle base and defines needle holes therein, the needle holes positioned to be aligned with the needle passer devices of the needle base. The needle holes extend through the threading base so as to extend through the guide slot of the threading base. With this arrangement, the first surface of the threading base is configured to receive the soft tissue thereon so that the soft tissue covers the needle holes.

In one embodiment, upon downward movement of the needle base, the needle passer devices move downward through the soft tissue so as to be positioned within the needle holes such that a tip portion of each of the needle passer devices is held at least partially within the needle holes. In another embodiment, with the tip portion positioned in the needle holes and upon upward movement of the needle base, a base portion of the needle passer devices separates from the tip portion of the needle passer devices to leave the loop portion of the first suture within each of the needle holes. In another embodiment, the passer device system further includes a threader positioned within the threader guide channel and partially positioned within the guide slot, one end portion of the threader coupled to a second suture such that the second suture is positioned within the slot entrance opening and extending partially within the guide slot. In still another embodiment, the threader is pushable through the threader channel and through the guide slot with the second suture coupled thereto such that the threader moves the second suture through the loop portion of the first suture positioned in each needle opening. In another embodiment, the first and second sutures are pulled taut such that the loop portion of the first suture is withdrawn from the needle holes and removed from the base portion of the needle passer devices such that the soft tissue is removable from the first surface of the threading base with the first and second sutures coupled thereto.

In another embodiment, the needle base is movable relative to the threading base with a threaded coupling that couples the needle base to the threaded base and facilitates movement of the needle base via rotation of a knob coupled to the needle base. In yet another embodiment, the tip portion is held to a needle tip guard positioned below the threading base, the needle tip guard configured to hold the tip portions thereto with an interference fit. In another embodiment, the tip portion includes a recess that holds the first suture to the tip portion to maintain the loop portion within the needle openings. In another embodiment, the tip portion defines a neck at least partially defining the recess to hold the loop portion thereto.

In another embodiment, the threader is driven through the threader guide channel and the guide slot with a rotatable gear coupled to the threading base. In another embodiment, the threader is elongated with multiple aligned openings sized and configured to correspond with teeth of the rotatable gear.

BRIEF DESCRIPTION OF THE SEVERAL VIEWS OF THE DRAWINGS

The foregoing and other advantages of the invention will become apparent upon reading the following detailed description and upon reference to the drawings in which:

FIG. 1 is a side view of a passer device with first and second sutures associated with the passer device, according to one embodiment of the present invention;

FIG. 2 is a front view of the passer device of FIG. 1, according to the present invention;

FIG. 3 is a perspective view of a passer device system with multiple passer members extending from a passer base member, depicting the first suture extending along each of the passer members, according to another embodiment of the present invention;

FIG. 4 is a perspective view of the passer device system with the first and second sutures associated therewith, depicting the multiple passer devices extending from the passer base member extending through soft tissue, according to another embodiment of the present invention;

FIG. 5 is a perspective view of the passer device system removed from the soft tissue, depicting multiple loops of the first suture extending from one side of the soft tissue with the second suture extending through the multiple loops, according to another embodiment of the present invention;

FIG. 6 is a top view of the first and second sutures moved to a taut position in the soft tissue, according to another embodiment of the present invention;

FIG. 12 is a perspective view of another embodiment of a passer device, depicting the first and second sutures associated with the passer device, according to the present invention;

FIG. 13 is a perspective view of another embodiment of a passer device, depicting first and second sutures associated with the passer device, according to another embodiment of the present invention;

FIG. 14 is a perspective view of another embodiment of a passer device, depicting the passer device pulling the first suture through soft tissue, according to the present invention;

FIG. 15 is a side view of another embodiment of a passer device system, depicting multiple passer devices extending through soft tissue facilitating alignment for the second suture to move through loops of the first suture, according to the present invention;

FIG. 16 is a side view of another embodiment of a passer device system, depicting multiple passer devices extending through soft tissue facilitating alignment for the second suture to move through loops of the first suture, according to the present invention;

FIG. 28A is a perspective view of a needle, depicting the needle with a loop suture extending laterally through a notch defined in the needle, according to another embodiment of the present invention;

FIG. 28B is a perspective view of the needle, depicting the needle separated into a base needle portion and a tip portion with the loop suture maintained in the notch, according to another embodiment of the present invention;

FIG. 30 is a perspective view of the passer device system, depicting the needles carrying the loop suture positioned through the soft tissue portion and through the threading base, according to another embodiment of the present invention;

FIG. 30A is a cross-sectional view of a portion of the passer device system taken along section line A-A of FIG. 30, according to another embodiment of the present invention;

DETAILED DESCRIPTION OF THE INVENTION

Figure 7:
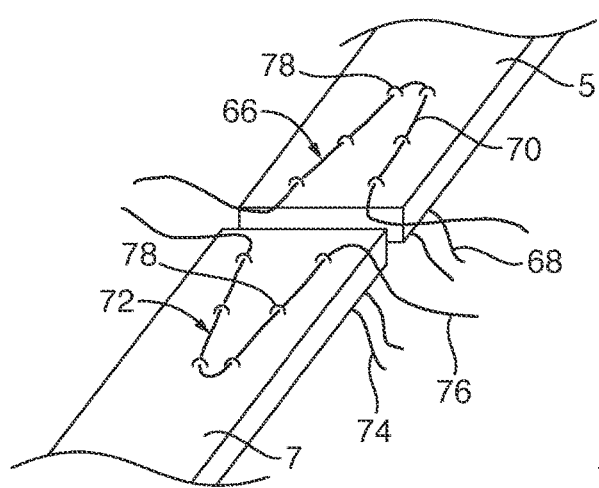
FIG. 7 is a perspective view of another embodiment of first and second sutures held in soft tissue, depicting a first tissue end portion and a second tissue end portion each with their own first and second sutures held therein, according to another embodiment of the present invention.

With reference to FIGS. 1-3, various embodiments are disclosed herein of a passer device system 10 and a method thereof. The passer device system 10 employs one or more sutures in a unique configuration for fixating soft tissue at a soft tissue repair site. Fixation of the soft tissue may be employed for fixating ruptures, tears or slices in soft tissue, such as tendon or ligament, for fixating one portion of soft tissue to another portion of soft tissue or fixating soft tissue to bone. In one embodiment, the passer device system 10 may employ multiple needles or passer devices 12 and a first suture 14 and a second suture 16 such that the passer devices 12 draw the first suture 14 through the soft tissue to form a loop 20 with each passer device 12 on one side of the soft tissue. The second suture 16 may then be passed through each of the loops 20 so that the passer devices 12 may then be withdrawn, and the first and second sutures 14, 16 moved to a taut position. With this arrangement, the passer device system 10 may be employed to implement an otherwise very difficult suture pattern.

As previously set forth, the passer device system 10 may include multiple needles or passer devices 12. As best shown in FIGS. 1 and 2, an enlarged view of a distal portion 22 of one of the passer devices 12 is depicted. The passer device 12 may be an elongated structure 24 in the form of a needle. The elongated structure 24 may extend with a length 26 between a proximal end (not shown) and a distal end 28 that defines a longitudinal axis 30 along the length 26. The distal end 28 may extend with a pointed free end 32 or tip. The distal portion 22 may include a distal end portion 34 that may extend with a tapered portion 36, extending toward the distal end 28 and to the pointed free end 32. The elongated structure 24 may extend with a radial external surface 38 such that the elongated structure 24 may extend with a circular cross-section, the cross-section extending laterally relative to the longitudinal axis 30.

The distal portion 22 of the passer device 12 may include a first recess 40 defined in the elongated structure 24. The first recess 40 may be positioned along the length 26 of the elongated structure 24. Further, the first recess 40 may be positioned proximally of the tapered portion 36 of the distal end portion 34 along the length 26 of the elongated structure 24. The first recess 40 may be sized and configured to removably hold the first suture 14 therein. The first recess 40 may be in the form of a notch, indent, or through hole defined in the elongated structure 24. The first recess 40 may extend in the elongated structure 24 to define an edge 42, such as a raised edge, the edge defining hook structure relative to the first recess. The hook structure may be sized and configured to hold and carry the first suture 14 therein so as to maintain the first suture 14 within the first recess 40.

The distal portion 22 of the passer device 12 may also include a second recess 44 defined in the elongated structure 24. The second recess 44 may be positioned proximally of the first recess 40 along the length 26 of the elongated structure 24. The second recess 44 may be in the form of a notch, indent or through hole defined in the elongated structure 24. The second recess 44 may be sized and configured to provide a void or gap relative to the elongated structure 24 for threading the second suture 16 along the second recess 44. Such second recess 44 may be positioned along the elongated structure 24 so that, upon the first suture 14 being positioned in the first recess 40, the second suture 16 may be moved along the second recess 44 so as to move through the loop 20 formed by the first suture 14. The first and second sutures 14, 16 interaction with the passer device 12 will be further described herein.

Now with reference to FIGS. 1 and 3-6, one embodiment of the passer device system 10 will now be described. With respect to FIGS. 3-4, the passer device system 10 may include multiple passer devices 12 or needles each of which may extend from a base member 46. The passer devices 12 may be fixed to the base member 46. In another embodiment, the passer devices 12 may be moveable along the corresponding axes 30 of each passer device 12. In one embodiment, the passer device system 10 may include six passer devices 12 or more. In another embodiment, the passer device system 10 may include four passer devices 12 or more. In another embodiment, the passer device system 10 may include at least five passer devices 12. In another embodiment, the passer device system 10 may include at least four passer devices 12.

The passer devices 12 may be positioned relative to each other in a pre-determined spaced relationship or predetermined configuration. Such predetermined configuration of the passer devices position relative to each other may be predetermined for a given type of soft tissue. In one embodiment, the passer devices 12 may be positioned in pairs, such as a first pair 48, a second pair 50, and a third pair 52, each pair spaced from each other and each passer device 12 within a given pair having a different spaced distance of an adjacently positioned pair of passer devices 12. For example, the first pair 48 may extend adjacent an inner side 54 of the base member 46 such that the passer devices 12 of the first pair 48 may be a first spaced distance 56 relative to each other. The second pair 50 may be spaced from the first pair 48 such that the passer devices 12 of the second pair 50 may be spaced from each other with a second spaced distance 58. Similarly, the third pair 52 may be spaced from the second pair 50 such that the passer devices 12 of the third pair 52 may be spaced from each other with a third spaced distance 60. The first spaced distance 56 may be larger than the second spaced distance 58 and the third spaced distance 60. The second spaced distance 58 may be larger than the third spaced distance 60. In another embodiment, adjacent pairs of spacer devices 12 do not have passer devices 12 that have a substantially common spaced distance from each other. In this manner, the passer devices 12 and their respective pairs may be positioned relative to the base member 46 in a pre-determined configuration. In another embodiment, adjacent pairs of passer devices 12 may be positioned so that passer devices 12 along a longitudinal length of soft tissue 3 may be positioned in a non-aligned manner.

With the passer devices 12 extending from the base member 46, the first suture 14 may be pre-positioned along the first recess 40 of each of the passer devices 12. For example, the first suture 14 may extend along one side of the base member 46 so as to extend along the first recess 40 of one passer device 12 of the first pair 48, then the first recess 40 of one passer device 12 of the second pair 50, and then the first recess 40 of one passer device 12 of the third pair 52. The first suture 14 may continue along the other side of the base member 46 so as to extend along the first recess 40 of another one of the passer devices 12 of the third pair 52, then the first recess 40 of another one of the passer devices 12 of the second pair 50 and then the first recess 40 of another one of the passer devices 12 of the first pair 48. In this manner, the first suture 14 may be pre-positioned along each of the passer devices 12 of the passer device system 10.

With the first suture 14 positioned along each of the passer devices 12 in, for example, a pre-assembled position, the passer devices 12 may be inserted through soft tissue 3, as depicted in FIG. 4. Further, FIG. 4 depicts the first suture 14 in dashed lines at portions where the first suture 14 extends through the soft tissue 3 and where the first suture 14 extends along an opposite side (underside or upper side depending on orientation of soft tissue 3 relative to the base member 46) of the loops 20 of the first suture 14. With the passer devices 12 being inserted through the soft tissue 3, a portion of the passer devices 12 and the first suture 14 may be exposed on one side of the soft tissue 3. Further, the first suture 14 may form the loop 20 along each of the passer devices 12 exposed on the one side of the soft tissue 3 such that multiple loops 20 of the first suture 14 may be disposed on the one side of the soft tissue 3, each loop 20 corresponding with one of the passer devices 12 of the passer device system 10.

Now with reference to FIGS. 4-5 in conjunction with FIGS. 1-2, the second suture 16 may be moved, as depicted by arrow 65, through each of the loops 20 formed by the first suture 14. In one embodiment, the second suture 16 may be passed along the second recess 44 of each passer device 12 so as to extend through each loop 20 of the first suture 14. For example, the loops 20 of the passer devices 12 may be defined as being adjacent a first side 62 of the base member 46 or a second side 64 of the base member 46. As such, in one embodiment, the second suture 16 may be passed consecutively through the loops 20 of the first pair 48, second pair 50 and third pair 52 of the passer devices 12 along or more adjacent the first side 62 of the base member 46. The second suture 16 may then continue to consecutively be passed through the loops 20 of the third pair 52, the second pair 50, and the first pair 48 of the passer devices 12 along or more adjacent to the second side 64 of the base member 46. In this manner, the second suture 16 may extend with a generally u-shape through each loop 20 (and second recess 44) of the passer devices 12 of the passer device system 10. Upon threading the second suture 16 through each of the loops 20 of the passer devices 12, the passer devices 12 and base member 46 may be withdrawn from or moved away from the soft tissue 3 and from being engaged with the first and second sutures 14, 16. As such, the first and second sutures 14, 16 may be positioned through and along the soft tissue 3, as depicted in FIG. 5, so that the first and second sutures 14, 16 are left in a unique coupling arrangement with the soft tissue 3. The first suture 14 and loops 20 may be pulled to a taut position so that the second suture 16 and ends of the loops 20 remain on the one side of the soft tissue 3, as depicted in FIG. 6. In another embodiment, one end of the first suture 14 may be pulled so that the slack is removed from the various portions along the length of the first suture 14 so that the first and/or second sutures 14,16 are moved to generally taut positions or positions where at least the slack is removed from between the interconnections of the first and second sutures 14, 16. In some embodiments, the slack from the first and/or the second sutures 14, 16 may be removed therefrom by pulling one end of the first suture 14 until, in the order along the first suture 14, a first loop is pulled through its tissue opening to pull the second suture 16 through the tissue opening to then create a loop in the second suture 16, the first suture 14 continuing to be pulled to pull the next loop and portion of the second suture 16 through its tissue opening to form another loop in the second suture 16, which may continue with the next ordered loops along the length of the first suture 14. In any of the processes of removing the slack from the first and second sutures 14, 16, the result is that the first and second sutures 14, 16 may be coupled to the soft tissue 3. Further, ends or end portions of the first and/or second sutures 14, 16 may be coupled to a bone anchor, for example, or to another portion of soft tissue, as set forth further herein.

With reference to FIG. 7, another embodiment is depicted for coupling first and second sutures to both a first tissue portion 5 and a second tissue portion 7. In this embodiment, the passer device system 10 depicted in FIG. 3 may be employed to first and second tissue portions 5, 7 so that the first and second tissue portions may be coupled together with a first set 66 of first and second sutures 68, 70 and a second set 72 of first and second sutures 74, 76. For example, the passer device system 10 of FIG. 3 may include an extended base member with additional pairs of passer devices so that a first set of passer devices may be associated with the first tissue portion 5 and a second set of passer devices may be associated with the second tissue portion 7, the first and second sets of passer devices positioned and extending from the base member in generally mirrored arrangement. In this embodiment, a physician may extend the passer devices with the respective first sutures 68, 74 associated with each of the first and second sets of passer devices through the first and second tissue portions 5, 7. The physician may then thread the second suture 70 of the first set 72 through loops 78 formed by the first set of passer devices on one side of the first tissue portion 5, similar to that previously described. The physician may then thread the second suture 76 through the loops 78 of the second set 72 formed by the passer devices on one side of the second tissue portion 7. The physician may then remove the passer device system to leave the first and second sets 66, 72 of first sutures 68, 74 and second sutures 70, 76 coupled to the respective first and second tissue portions 5, 7, as depicted in FIG. 7. The physician may then place the first and second sutures of the first and second suture sets 66, 72 in a taut position, coupling suture end portions together using crimps or knots to, thereby, couple the first and second tissue portions 5, 7 together.

Figure 8:
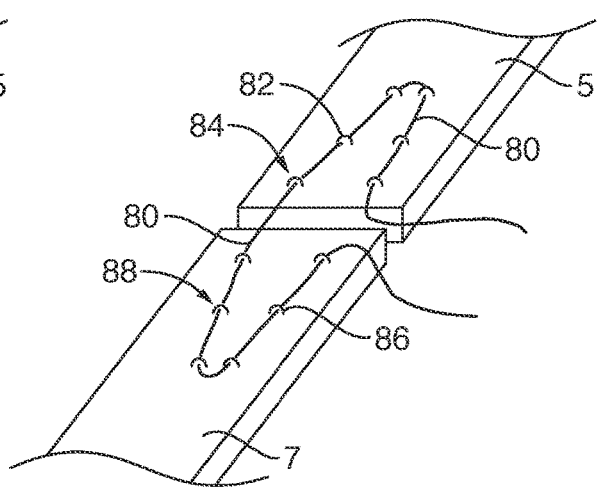
FIG. 8 is a perspective view of another embodiment of first and second sutures coupled to a first tissue end portion and a second tissue end portion, depicting a single second suture employed with the first and second tissue end portions, according to another embodiment of the present invention.

With reference to FIG. 8, another embodiment for coupling suture to first and second tissue portions 5, 7 is depicted. The suture coupling of this embodiment may be employed with a similar passer device system as described relative to FIG. 7, except in this embodiment a single suture strand may be employed as a second suture 80 for coupling to the first and second tissue portions 5, 7. For example, loops 82 of a first suture 84 may be formed on one side of the first tissue portion 5 and loops 86 of another first suture 88 may be formed on one side of the second tissue portion 7 by employing the passer device system, as previously described. The second suture 80 may then be threaded through the loops 82 on one side of the first tissue portion 5 and then threaded through the loops 86 of one side of the second tissue portion 7. The ends or end portions of the sutures may then be coupled together to, thereby couple the first and second tissue portions 5, 7 together. In another embodiment, a single first suture may be employed for forming the loops on one side of the first and second tissue portions 5, 7. In still another embodiment, one or both of the first and second sutures may extend as a continuous suture loop (without ends).

Figure 9:
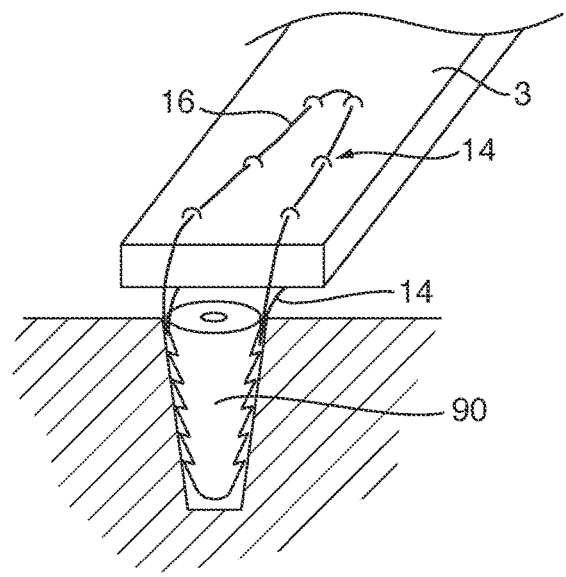
FIG. 9 is a perspective view of another embodiment of first and second sutures coupled to a first tissue end portion and a bone anchor, according to another embodiment of the present invention.

With reference to FIGS. 3-6 and 9, another embodiment for coupling first and second sutures 14, 16 to a soft tissue 3 is provided. In this embodiment, the first and second sutures 14, 16 may be coupled to soft tissue 3 with the passer device system 10, similar to that described relative to FIGS. 3-6. Upon the first and second sutures 14, 16 being coupled to the soft tissue 3, ends or end portions of the first and second sutures 14, 16 may be coupled to a bone anchor 90. In this manner, the passer device system 10 may be employed for coupling first and second sutures 14, 16 to soft tissue 3 to then be coupled to the bone anchor 90, as depicted in FIG. 9.

Figure 10:
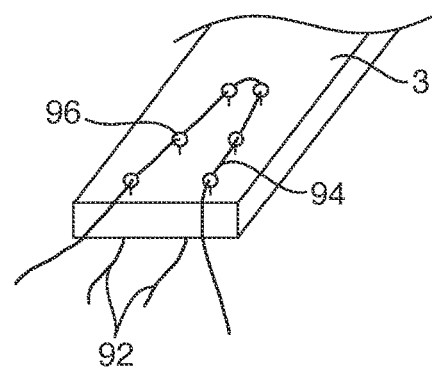
FIG. 10 is another embodiment of first and second sutures coupled to a first tissue end portion, depicting the first suture having pre-formed loops therein, according to another embodiment of the present invention.

With reference to FIG. 10, another embodiment of a first suture 92 and a second suture 94 coupled to soft tissue 3 is provided. In this embodiment, the first suture 92 may be coupled to multiple passer devices, similar to the first suture 14 depicted in FIG. 3, except the first suture 92 of this embodiment may include pre-formed loops 96 along a length of the first suture 92. Such pre-formed loops 96 may be positioned and held in the first recess 40 of each corresponding passer device 12 such that the passer devices may extend through soft tissue 3, similar to that depicted in FIGS. 1 and 4, to then expose the pre-formed loops 96 on one side of the soft tissue 3. The physician may then thread the second suture 94 through each of the pre-formed loops 96 and the passer devices may be withdrawn from the soft tissue 3, similar to that depicted in previous embodiments.

Figure 11:
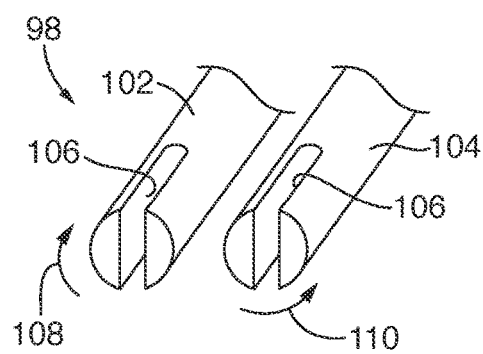
FIG. 11 is a perspective view of a portion of a tightening tool that may be employed with the first or second sutures, according to another embodiment of the present invention.

With reference to FIG. 11, one embodiment of a tightening tool 98 sized and configured to place first and second sutures, described in previous embodiments, in a taut position is provided. The tightening tool 98 may include a first holding end portion 102 and a second holding end portion 104. Each of the first and second holding end portions 102, 104 may include a notch 106 defined in ends thereof. Loose end portions of the first and/or second sutures may be positioned in the notches 106, after which, the first and second holding end portions may be simultaneously rotated in opposite directions as depicted by arrows 108, 110. For example, the first holding end portion 102 may rotate clockwise, as shown by arrow 108. The second holding end portion 104 may rotate counter-clockwise, as shown by arrow 110. The rotation of the first and second holding end portions 102, 104 may be employed with a rotatable knob (not shown), for example, and may include a slip clutch (not shown) associated therewith to minimize and control the amount of tension placed on the first and/or second sutures being moved to the taut position with the tightening tool 98. Once in a controlled taut position, the first and second sutures may be tied off or crimped to maintain the tension placed on the first and second sutures.

With reference to FIG. 12, the passer devices 12 of the passer device system 10 (FIG. 3) may extend with various configurations. For example, in another embodiment, a passer device 112 may extend with similar structural characteristics as the passer device depicted in FIGS. 1 and 2. The passer device 112 of this embodiment may extend with an elongated structure 114 with a flat profile extending along a longitudinal axis 116 defined along a length 118 of the elongated structure 114. The passer device 112 may include a distal portion 120 with a tapered portion 122 along a distal end portion 124 of the passer device 112 that may extend to a pointed free end 126. The distal portion 120 may include a first recess 128 sized and configured to hold a first suture 130, similar to the previous embodiments. The distal portion 120 of the passer device 112 may include a second recess 132, the second recess 132 sized and configured to facilitate threading a second suture 134 along the second recess 132. In this embodiment, the second recess 132 may be formed along the elongated structure 114 with the elongated structure 114 extending with one or more bends or curved portions along the length 118 of the elongated structure 114. In other words, the elongated structure 114 may extend with a flat profile with one or more bends or curved portions transversely extending relative to the longitudinal axis 116 of the elongated structure 114.

With reference to FIG. 13, another embodiment of a passer device 136 that may be employed with a passer device system, similar to that described in the embodiment described in FIG. 3. The passer device 136 of this embodiment may extend with a curved portion 138 along a distal portion of the passer device 136 with a tapered portion 140 extending to a pointed tip 142. The distal portion of the passer device 136 may include a recess 144 defined therein, the recess 144 having an edge 146 such that the recess may be sized and configured to hold a first suture 148. Further, with the first suture 148 positioned along the recess 144, the first suture 148 may form a loop 150 for receiving a second suture 152 therethrough, similar to previous embodiments.

Now with reference to FIG. 14, another embodiment of a passer device 154 is provided. In this embodiment, the passer device 154 may include a distal portion 156 with a tapered portion 158 extending to a pointed tip 160 and a recess 162 defined in the passer device 154. The recess 162 may be positioned adjacent the tapered portion 158 and may define an edge 164 having a hooked structure. The edge 164 may be positioned adjacent the recess 162 such that the first suture 166 may be held within the recess 162 in manner to facilitate pulling a first suture 166 through soft tissue 3. For example, the passer device 154 may be inserted through the soft tissue 3 so as to grab the first suture 166 and then be withdrawn from the soft tissue 3 to pull the first suture 166 through an insertion hole 9, as depicted by arrow 169, formed by the previously inserted passer device 154. Upon pulling the first suture 166 through the soft tissue 3, the first suture 166 may extend to define a loop 168 on one side of the soft tissue 3 so that a second suture may be passed through the loop 168, similar to that set forth in previous embodiments.

With reference to FIG. 15, another embodiment of a passer device system 170 is provided. This embodiment of the passer device system 170 may include passer devices similar to that employed to that described in FIGS. 3-6, except passer devices 172 of this embodiment may be oriented at predetermined angles so as to align a second recess 174 defined in each of the passer devices 172. With such alignment of the second recess 174 of multiple ones of the passer devices 172, a second suture 176 may be threaded through loops defined in a first suture 178 carried by the passer devices 172 in a more simplified manner. Further, in this embodiment, the passer devices 172 may be moveable along a longitudinal axis 180 of a given passer device 172 with the first suture 178 attached to each respective passer device 172. Upon sequentially or simultaneously extending each of the passer devices 172 through the soft tissue 3, the second suture 176 may then be threaded through the substantially aligned second recesses 174 and loops formed on one side of the soft tissue 3 with the passer devices 172. The passer devices 172 may then be withdrawn from the soft tissue 3 to thereby, leave the first suture 178 and the second suture 176 coupled to the soft tissue 3, similar to that depicted in FIG. 6.

With reference to FIG. 16, another embodiment of a passer device system 182 is provided. This embodiment is similar in concept as that depicted in FIG. 15, except in this embodiment, passer devices 184 may extend with a curved portion 186, similar to the passer device depicted in FIG. 13. In this embodiment, the passer devices 186 may extend through the soft tissue 3 such that loops of the first suture (not shown) formed with the passer devices 184 on one side of the soft tissue 3 may be aligned such that a second suture 188 may be more readily threaded through the loops in a simplified manner, similar to the previous embodiment.

Figure 17:
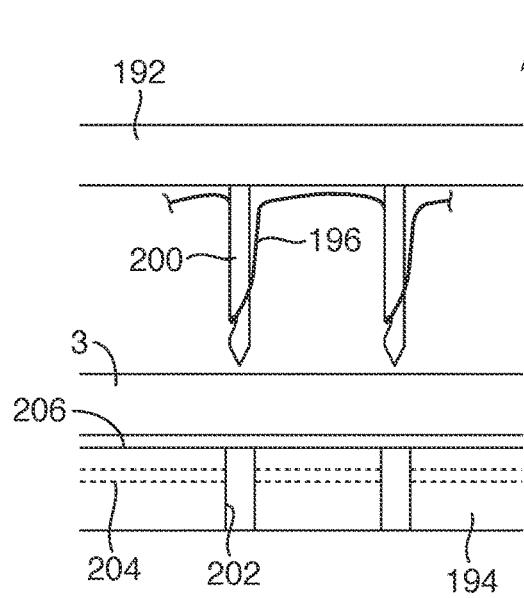
FIG. 17 is a simplified side view of another embodiment of a passer device system, depicting passer devices extending from a first base member with soft tissue positioned on a second base member, according to the present invention.
Figure 18:
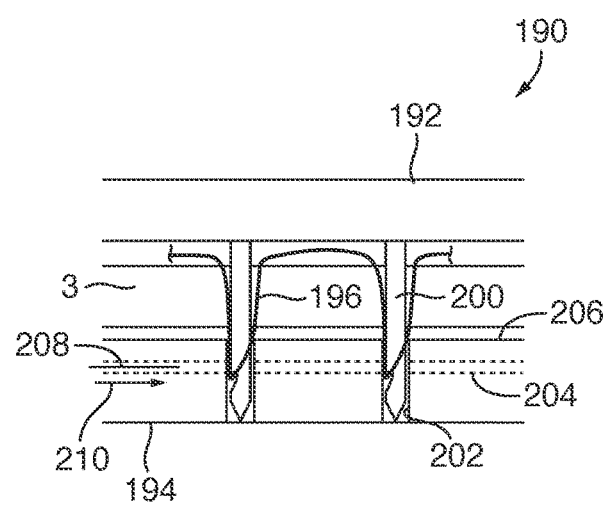
FIG. 18 is a simplified side view of the passer device system of FIG. 17, depicting the passer devices extending through soft tissue and slots in the second base member, according to another embodiment of the present invention.
Figure 19:
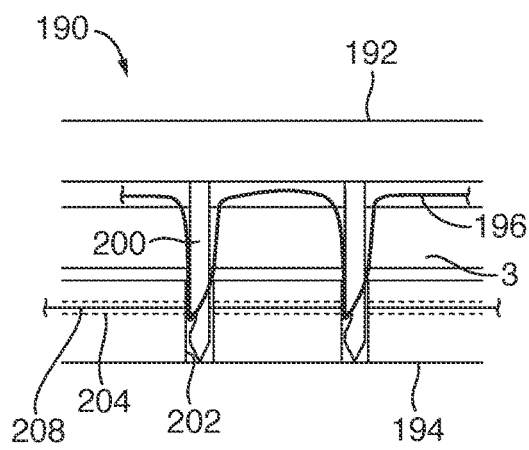
FIG. 19 is a simplified side view of the passer device system of FIG. 17, depicting a second suture moved through the second base member and through loops of the first suture associated with each of the passer devices, according to another embodiment of the present invention.
Figure 20:
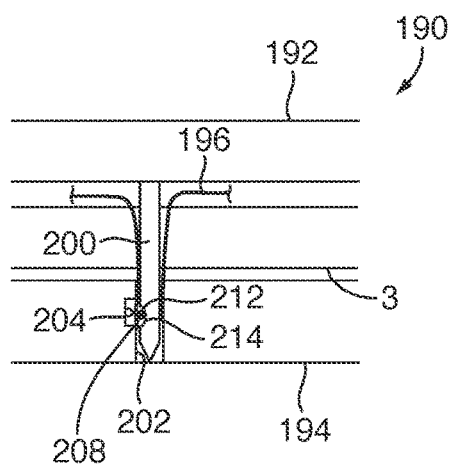
FIG. 20 is a simplified front view of the passer device system of FIG. 17, depicting a channel defined in the second base member and the second suture extending through one of the loops of the first suture, according to another embodiment of the present invention.

Now with reference to FIGS. 17-21, another embodiment of a passer device system 190, in simplified form, is provided. The passer device system 190 may include a first base member 192 and a second base member 194. The first base member 192 may include a first suture 196 engaged with multiple passer devices 200, the multiple passer devices 200 extending from the first base member 192, similar to that depicted in FIG. 3. The second base member 194 may include slots 202 defined therein that may be sized and configured to receive corresponding ones of the passer devices 200 such that the slots 202 may be aligned with the passer devices 200. Further, the second base member 194 may include a channel 204 extending through the second base member 194 which may communicate with the slots 202, as depicted in FIGS. 17 and 20.

Figure 21:
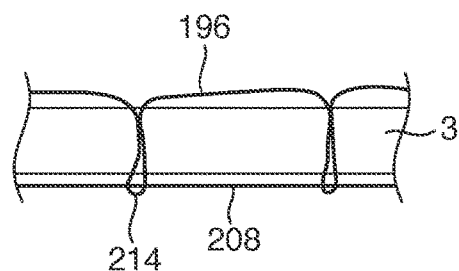
FIG. 21 is a simplified side view of the first and second sutures coupled to the soft tissue, depicting the passer device system of FIG. 19 removed from the soft tissue, according to another embodiment of the present invention.

With respect to FIGS. 17 and 18, the passer device system 190 may be employed by placing soft tissue 3 over an upper surface 206 of the second base member 194. The first base member 192 may then be moved toward the soft tissue 3 so that the passer devices 200 and the first suture 196 engaged with the passer devices 200 extends through the soft tissue 3 and into the slots 202 defined in the second base member 194. At this stage, a second suture may then be threaded through the channel 204, as indicated by arrow 210. With reference to FIGS. 19-20, such channel 204 coincides with a second recess 212 (see also second recess 44 of FIGS. 1 and 2) defined in the passer devices 200 as well as communicates with the slots 202 defined in the second base member 194. As the physician threads the second suture 208 through the channel 204, the second suture 204 moves past the second recess 212 so as to extend through loops 214 (FIG. 21) of the first suture 196. Upon the second suture being fully threaded through the channel 204, the first base member 192 may be withdrawn so that the passer devices 200 slide out of the soft tissue 3. The second base member 194 may also be withdrawn relative to the soft tissue 3, leaving the first and second sutures 196, 208 being coupled to the soft tissue 3, as depicted in FIG. 21. In this manner, the passer device system 190 may employ first and second base members 192, 194 and passer devices 200 for coupling the first and second sutures 196, 208 to the soft tissue 3.

Figure 22:
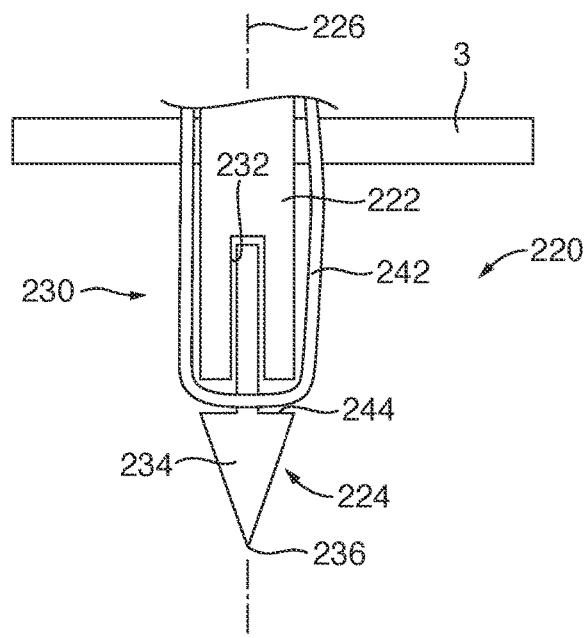
FIG. 22 is a side view of another embodiment of a passer device, depicting the passer device extending through soft tissue and associated with a first suture, according to the present invention.
Figure 23:
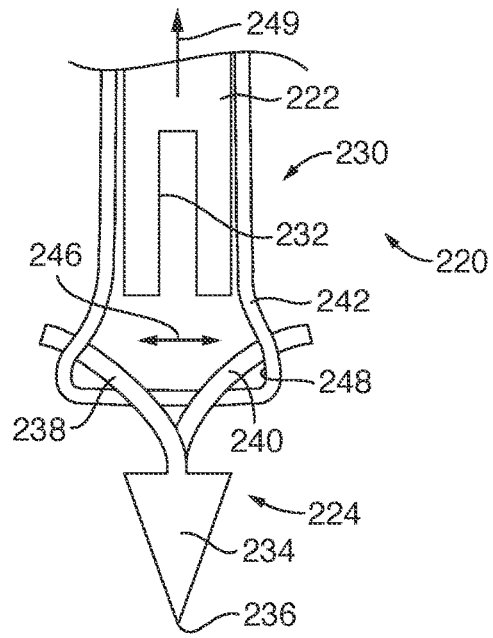
FIG. 23 is a side view of the passer device of FIG. 22, depicting the passer device having a break-away feature with a tip of the passer device self-expanding to form a loop in the first suture, according to the present invention.

Now with reference to FIGS. 22 and 23, another embodiment of a passer device 220 sized and configured to pass through soft tissue 3 is provided. In this embodiment, the passer device 220 may include one or more break-away features. For example, the passer device 220 may include a stem or body 222 with a tip portion 224. The body 222 may define a longitudinal axis 226 and may be fixed to a first base member 228 (FIG. 24) or may be moveable along the axis 226 to be driven and withdrawn along the axis 226 relative to the first base member 228. The tip portion 224 may be removably coupled to a distal end portion 230 of the body 222 such that the body 222 may define a notch 232 in a distal end of the body 222. The tip portion 224 may include a tip 234 with a pointed end 236 with one or more arms extending proximally from the tip 234. The one or more arms may include a first arm 238 and a second arm 240, each movable between first and second positions. The first position of the first and second arms 238, 240 may be constrained positions that may be held within the notch 232 defined adjacent the distal end of the body 222. The second position of the first and second arms 238, 240 may be self-expanded, outward extending positions so as to extend with a v-configuration. Such tip 234 and first and second arms 238, 240 may be formed of an elastic material, such as Nitinol, or spring steel, for example, or any other suitable material sized and configured to self-expand from a constrained position. The first and second arms 238, 240 may move to the expanded second position, upon the tip portion 224, being released or breaking away from the body 222 of the passer device 220. As in previous embodiments, the passer device 220 may include a first suture 242 extending along the body 222 and along a recess 244 defined adjacent the distal end of the body 222 of the passer device 220. Upon the tip portion 224 being released from the body 222, the first and second arms 238, 240 may move to the expanded second position such that the first and second arms 238, 240 move outward, as shown by arrows 246, so as to expand the first suture 242 and form a loop structure 248 or loop. Once such loop structure 248 in the first suture 242 is formed by the first and second arms 238, 240, the body 222 of the passer device 220 may be withdrawn, as shown by arrow 250. Such two-piece break-away passer device 220 may provide a simplified arrangement for threading a second suture 252 (see FIGS. 26-27) through the looped structures 248 associated with multiple passer devices 220.

With reference to FIGS. 24-27, a passer device system 250 that may employ multiple ones of the two-piece passer devices 220, as set forth in FIGS. 22-23, will now be described. Similar to previous embodiments, the passer device system 250 of this embodiment may include the first base member 228 and a second base member 252. For simplification purposes, only two passer devices 220 are shown extending from the first base member 228, but the first base member 228 may include, for example, at least four passer devices 220 or four, five, six, eight, ten, or twelve passer devices 220 or more, depending upon the desired configuration for coupling the first suture and a second suture 254 to soft tissue 3.

Figure 24:
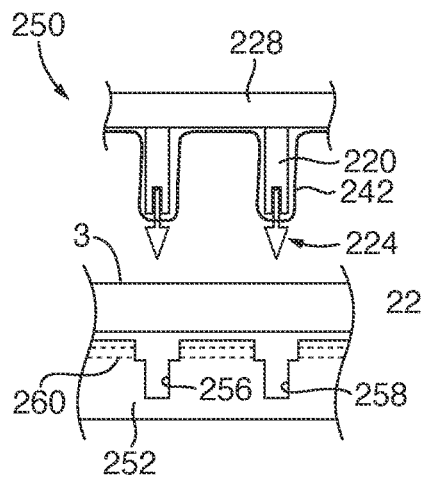
FIG. 24 is a side view of another embodiment of a passer device system, depicting multiple passer devices extending from a first base and soft tissue positioned over a second base of the passer device system, according to the present invention.

As depicted in FIG. 24, soft tissue 3 may be positioned over the second base member 252. The second base member 252 may include slots corresponding with the passer devices 220 extending from the first base member 228, for example, a first slot 256 and a second slot 258 defined in the second base member 252. Such first and second slots 256, 258 may be sized and configured to receive the tip portion 224 of corresponding ones of the passer devices 220. Further, the second base member 252 may include a channel 260 extending across the second base member 252 that may communicate and correspond with the first and second slots 256, 258 defined in the second base member 252. Such channel 260 may be sized and configured to feed or thread the second suture 254 therethrough, similar to that described and depicted in previous embodiments. Upon the physician positioning soft tissue 3 over the second base member 252, the first base member 228 may be moved toward the second base member 252 so that the passer devices 220 extend through the soft tissue 3 and the tip portion 224 of the passer devices 220 are positioned in respective first and second slots 256, 258, as depicted in FIG. 25.

Figure 25:
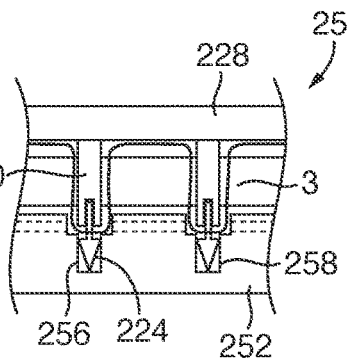
FIG. 25 is a side view of the passer device system of FIG. 24, depicting the passer devices extending through the soft tissue and tips of the passer devices positioned within slots of the second base member, according to another embodiment of the present invention.
Figure 26:
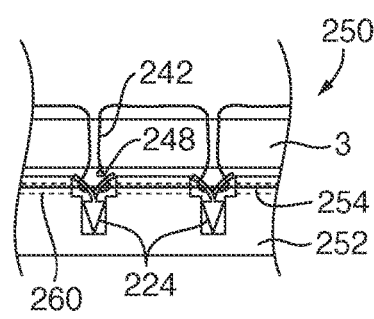
FIG. 26 is a side view of the passer device system of FIG. 24, depicting stems of the passer devices removed with tails of the tips forming loops in the first suture and depicting a second suture threaded through the loops of the first suture, according to another embodiment of the present invention.
Figure 27:
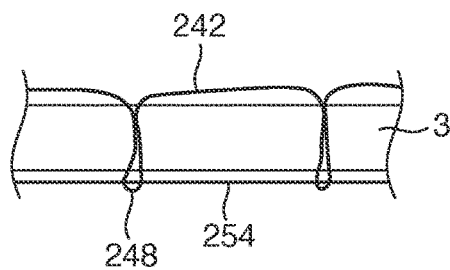
FIG. 27 is a simplified side view of first and second sutures coupled to soft tissue with the passer device system moved of FIG. 26 removed from the soft tissue, according to another embodiment of the present invention.

With respect to FIGS. 25-26 and in conjunction with FIGS. 22 and 23, upon the tip portion 224 of the passer devices 220 being positioned within the respective first and second slots 256, 258 of the second base member 252, the first base member 228 may be moved away from the second base member 252. Movement of the first base member 228 also may move the body 222 of the passer devices 220 away from the second base member 252, leaving the tip portion 224 of the passer devices 220 within the respective first and second slots 256, 258. As previously described, upon first and second arms 238, 240 being removed from the notch 232 of the body 222 of the passer devices 220, the first and second arms 238, 240 may move to the second position or expanded position. In this expanded position, the first and second arms 238, 240 expand and hold the first suture 242 in an open position, forming the loop structure 248 with the first suture 242 adjacent the tip portion 224 and within the first and second slots 256, 258. At this juncture, the physician may thread the second suture 254 through the channel 260 which may be aligned with the loop structure 248 of the first suture 242 adjacent the tip portion 224, as depicted in FIG. 26. Once the second suture 254 has passed through each loop structure 248 within the given slots defined in the second base member 252, the second base member 252 with the tip portions 224 may be moved relative to the soft tissue 3, as depicted in FIG. 27. With this arrangement, the two-piece passer devices 220 may be employed for coupling first and second sutures 242, 254 to soft tissue 3. Further, as will be readily understood by one of ordinary skill in the art and as described in the various embodiments herein, the first and second sutures 242, 254 may be coupled to soft tissue 3 at a soft tissue repair site for fixating one piece of soft tissue to another piece of soft tissue or for fixating one piece of soft tissue 3 to bone with, for example, a bone anchor 90 (FIG. 9).

Now with reference to FIGS. 28-36, another embodiment of a passer device 270 or, otherwise referenced as a passer device system or delivery tool, for coupling first and second sutures 272, 274 to soft tissue is provided. The passer device 270 of this embodiment may be employed in a similar manner as the embodiments of the passer device depicted and described relative to FIGS. 17-21 and also in FIGS. 22-27. Although not depicted in this embodiment, the passer device 270 may be in the form of including a cartridge with a cartridge housing.

Figure 28:
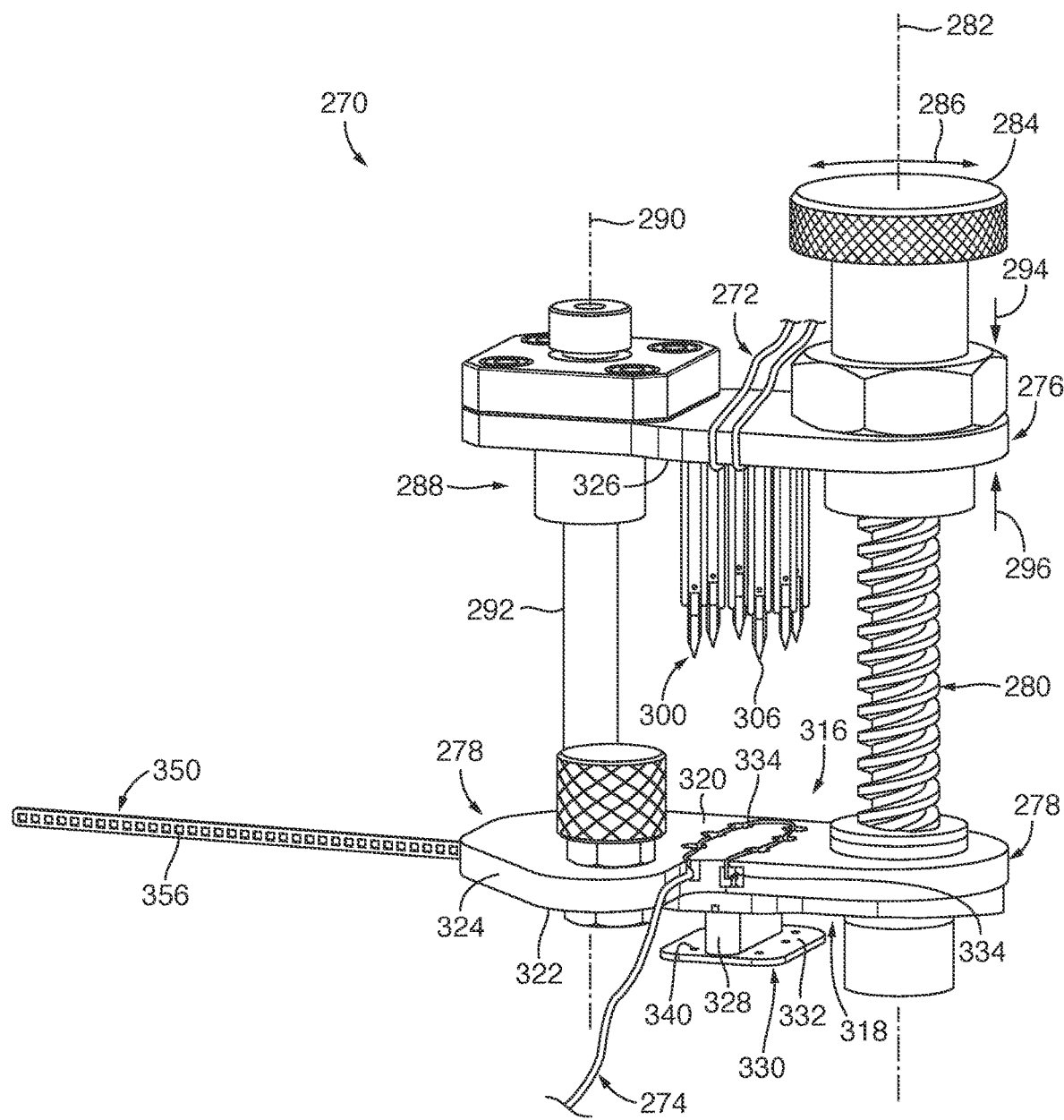
FIG. 28 is a perspective view of another embodiment of a passer device system, depicting needles extending downward from a needle base toward a threading base, according to the present invention.

With reference to FIG. 28, similar to the previous embodiments, the passer device 270 may include opposing base structures, such as a needle base 276 and a threading base 278. The needle base 276 and the threading base 278 may be coupled together and movable relative to each other. The needle base 276 may be coupled to the threading base 278 with a threaded coupling rod 280 that may be rotatable to move the needle base 276 closer or away from the threading base 278. The threaded coupling rod 280 may define an axis 282. Such movement of the needle base 276 relative to the threading base 278 may be employed by rotating the threaded coupling rod 280 with a knob 284 or lever like structure about the axis 282, either clockwise or counter-clockwise, as shown by rotational arrow 286. Further, the passer device 270 may include guide structure 288 to stabilize and support the movement of the needle base 276 relative to the threading base 278. The guide structure 288 may define a guide axis 290 with a guide rod 292, one end of the guide rod 292 fixed to the threading base 278 with the needle base 276 slidable over an elongated length of the guide rod 292 to support and guide the needle base 278. In this manner, clockwise rotation of the knob 284 may move the needle base 276 closer to the threading base 278, as shown by downward arrow 294, such that the needle base 276 may move downward and over the threaded coupling rod 280 and the guide rod 292. Further, counter-clockwise rotation of the knob 284 may move the needle base 276 further away from the threading base 278, as shown by arrow 296, such that the needle base 276 may move upward and along the threaded coupling rod 280 and the guide rod 292. In one embodiment, the axis 282 of the threaded coupling rod 280 may extend parallel relative to the guide axis 290 defined by the guide rod 292.

With reference to FIGS. 28, 28A, and 28B, similar to previous embodiments, the needle base 276 may include multiple needles 300 extending from the needle base 276 toward the threading base 278, the needles 300 each having an elongated length 302 and each defining a needle axis 303 such that the needle axis 303 may extend along and parallel with the elongated length 302 of the needles 300. In one embodiment, the needles 300 may be fixed to the needle base 276 such that the needles 300 may be positioned, and spaced relative to each other, to extend from the needle base 276 in a predetermined configuration. Further, each needle 300 may extend with the elongated length 302 between a base end 304 and a pointed end 306, the base end 304 being fixed to the needle base 376. Further, each of the needles 300 may include a base portion 308 and a tip portion 310, the tip portion 310 removable from the base portion 308 (as depicted in FIG. 28B). The transition between the tip portion 310 and the base portion 308 may at least partially define a notch 312, the notch defined at least partially in the tip portion 310. As in previous embodiments, the passer device 270 may include the first suture 272, which also may be referenced as a loop suture. The first suture 272 or loop suture may extend along a length of the base portion 308 of each of the needles 300 to form a loop 314 adjacent the notch, similar to that depicted in FIG. 22 or 23. In this manner, the first suture 272 may extend and wind along portions of each of the needles 300 to form the loop 314 adjacent the notch 312 defined in each needle 300. Such notch 312 may define a neck 315 to assist in removably holding the first suture 272 in the notch 312 of the tip portion 310.

Figure 29:
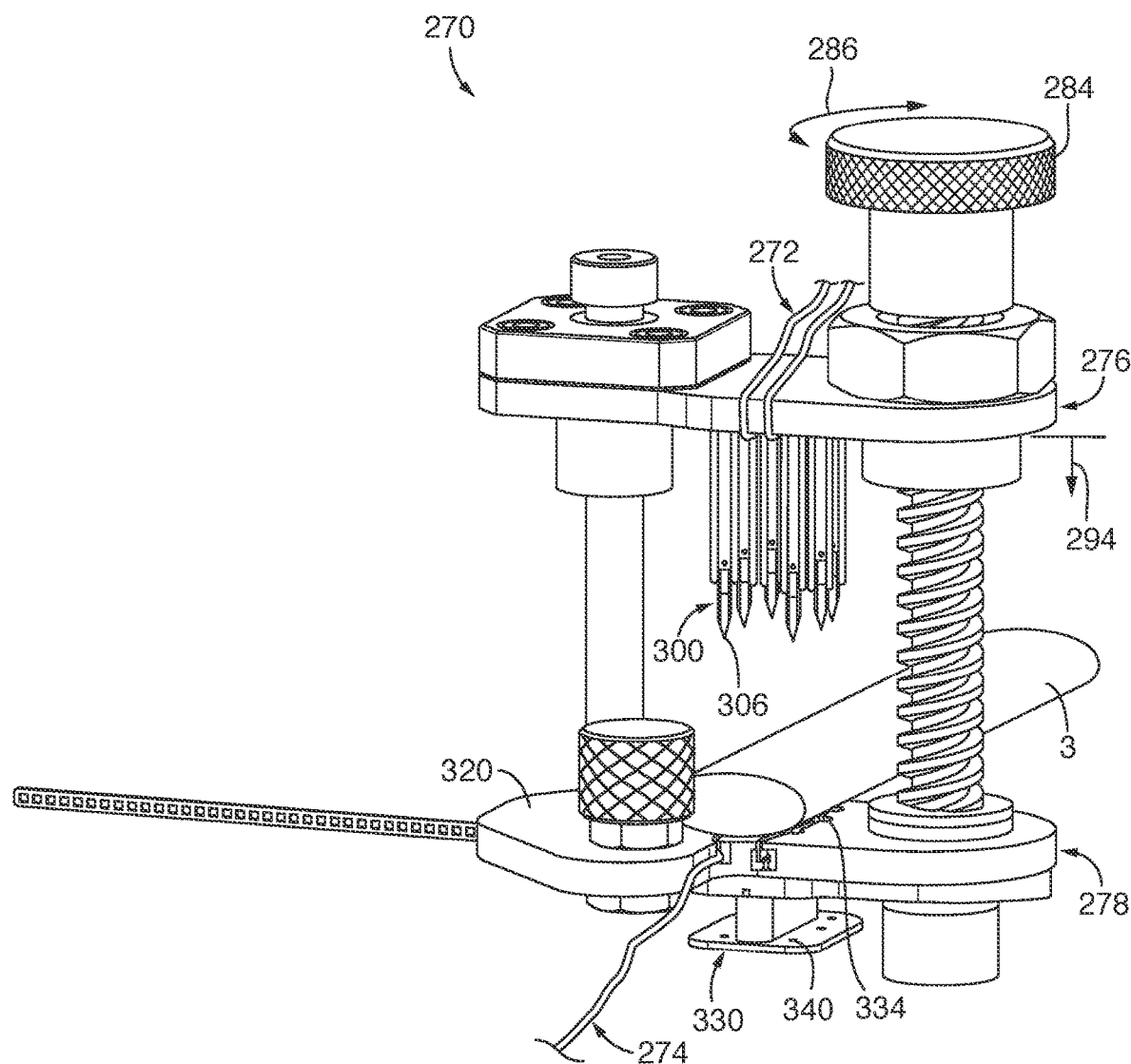
FIG. 29 is a perspective view of the passer device system, depicting a soft tissue portion positioned over the threading base of the passer device system, according to another embodiment of the present invention.

With reference again to FIG. 28, the threading base 278 may extend with opposite first and second sides 316, 318, the first side 316 extending with a first surface 320 and the second side 318 extending with a second surface 322. The first surface 320 extending directly to a peripheral surface 324. The peripheral surface 324 may orthogonally extend relative to the first surface 320. The first surface 320 may face a needle base surface 326, the base end 304 of the needles 300 being fixed to and extending from the needle base surface 326 (see FIG. 28A). Depending upon the orientation of the passer device 270, the first surface 320 may be an upward facing surface that may be sized and configured to receive a soft tissue portion, such as a tendon portion 3 (FIG. 29). The threading base 278 may include an extension 328 extending from the second side 318 of the threading base 278, the extension 328 supporting a needle tip guard 330. The needle tip guard 330 may extend with a guard surface 332, which may face toward the second side 318 of the threading base 378. Further, the needle tip guard 330 may be a generally flat structure.

Figure 31:
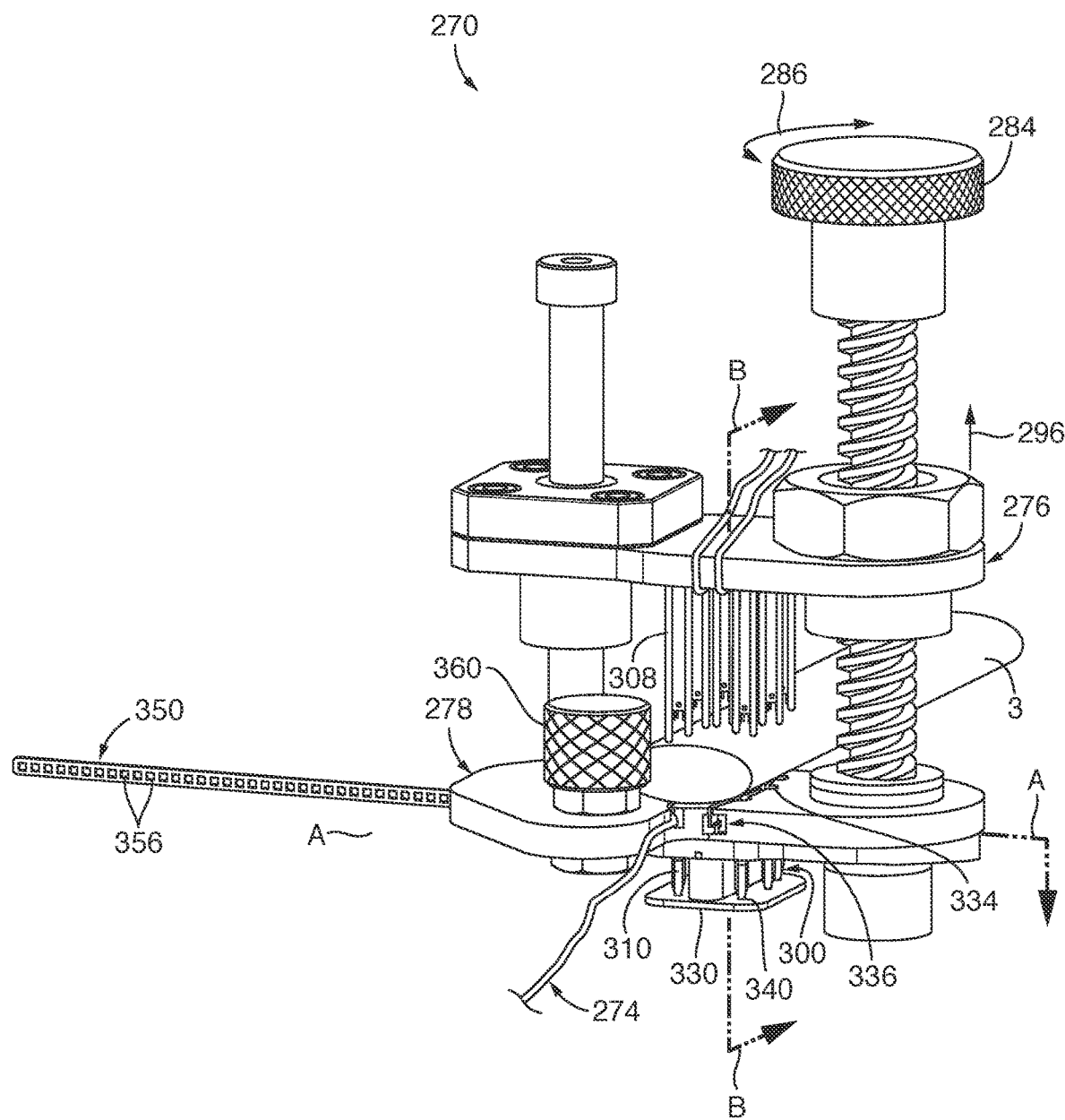
FIG. 31 is a perspective view of the passer device system, depicting the needles with a base portion separated from a tip portion of the needles, according to another embodiment of the present invention.
Figure 31A:
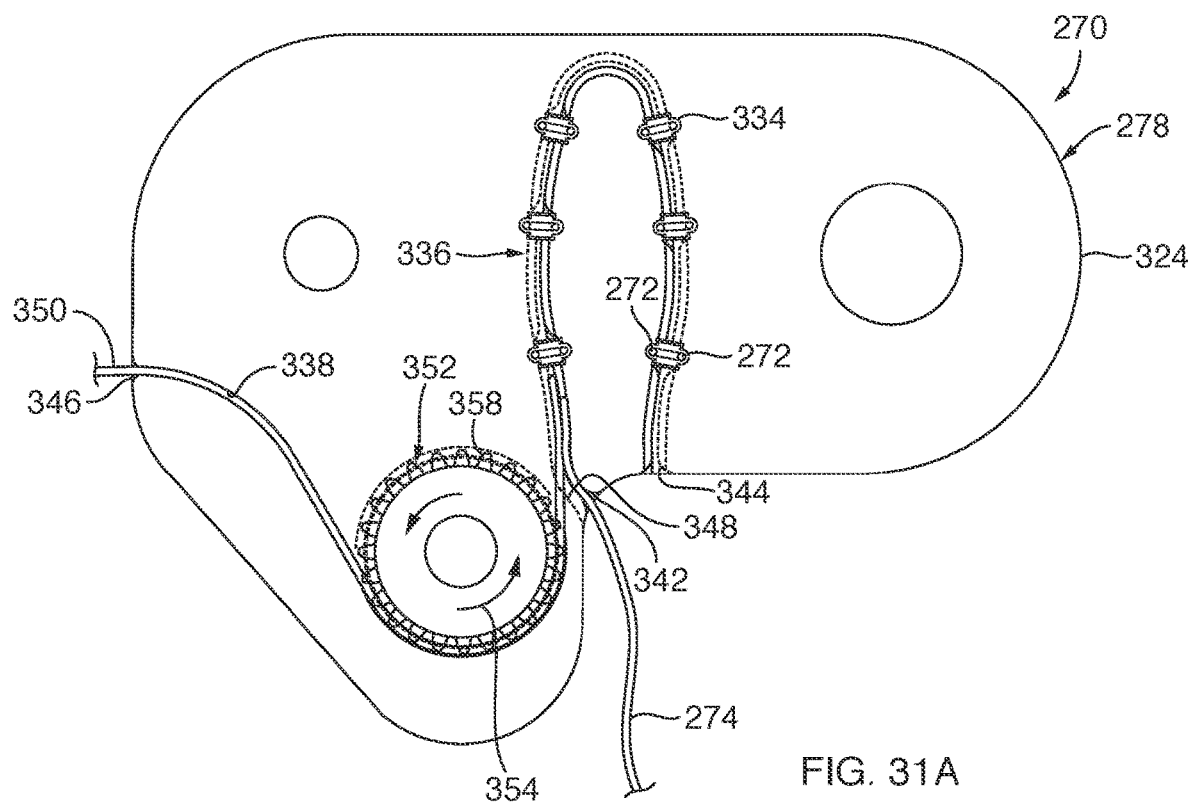
FIG. 31A is a cross-sectional view of the passer device system taken from section line A-A of FIG. 31, depicting a threader coupled to one end of a threading suture within a suture guide slot in a preliminary first position, according to another embodiment of the present invention.

With respect to FIGS. 28 and 31A, the threading base 278 may include needle holes 334, a suture guide slot 336, and a threader guide channel 338, each defined in the threading base 278. For example, the needle holes 334 may be defined in the first surface 320 and extend through the threading base 278 to the second side 318 of the threading base 278. Each one of the needle holes 334 may be aligned with one of the needles 300 such that the needles 300 may be inserted through the needle holes 334. Further, the guard surface 332 may define tip openings 340 therein such that each of the tip openings 340 may be aligned to correspond with one of the needle holes 334 and the pointed end 306 of one of the needles 300. In this manner, the needle holes 334 may be sized and configured to receive each of the needles 300 of the needle base 276.

The suture guide slot 336 may extend to define entrance and exit openings 342, 344 of the suture guide slot 336 so as to each be defined in the peripheral surface 324 of the threading base 278. Further, the suture guide slot 336 may be defined within the threading base 278 so as to extend through each of the needle holes 334 and between the entrance and exit openings 342, 344. In other words, the suture guide slot 336 extends through the threading base 278 such that the guide slot 336 communicates with each of the needle holes 334. Further, the threader guide channel 338 may extend through the threading base 278 between a threader entrance 346 and a threader exit 348. The threader entrance 346 may be defined in the peripheral surface 324 of the threading base 278 and the threader exit 348 may be defined adjacent the entrance opening 342 of the suture guide slot 336 along a surface defining the suture guide slot 336. In other words, the threader guide channel 338 may communicate with the suture guide slot 336. Further, the threader guide channel 338 may extend along a gear positioned in the threading base 278. The threader guide channel 338 may be sized and configured to hold a threader 350 therein. Further, the threader 350 may be engaged with the gear 352 so that rotational movement of the gear 352, as shown by rotational arrow 354, may move the threader 350 through the threader guide channel 338 and into the suture guide slot 336. Also, the threader 350 may be coupled to one end of the second suture 274 so that the threader 350 can be manipulated via rotation of the gear 352 to, in turn, manipulate the second suture 274, discussed further herein. In one embodiment, the threader 350 may extend with multiple threader openings 356 defined therein, the threader openings 356 being aligned relative to each other and sized and configured to be engaged with teeth 358 of the gear 352. The threader 350 may extend with a certain degree of stiffness so that rotation of the gear 352 will push the threader 350 through the threader guide channel 338 and through the suture guide slot 336. In this manner, the threader 350 may act as a driver for moving the second suture 374 through the threading base 278, discussed further herein. The threader 350 may be formed of a metallic material, such as Nitinol, or any other suitable metallic material, or the threader 350 may be formed of a suitable polymeric material.

Now with reference to FIGS. 28-36, a method of employing the passer device 270 to couple the first and second sutures 272, 274 to a tendon portion 3 will now be described. With respect to FIGS. 28 and 29, the tendon portion 3 may be positioned over the first surface 320 of the threading base 278 such that the tendon portion 3 directly overlies the needle holes 334 defined in the first surface 320 of the threading base 278. As such, the tendon portion 3 may be positioned between the needle base 276 and the threading base 278 with the needles 300 positioned and oriented to extend downward toward the threading base 278 and the tendon portion 3 positioned thereon.

With respect to FIGS. 29, 30 and 30A, with the tendon portion 3 positioned over the threading base 278, the needle base 276 may move downward by rotating the knob 284, as shown by the rotational arrow 286, to move the needle base 276 downward toward the threading base 278, as shown by arrow 294. Such downward movement of the needle base 276 may continue so that the needles 300 move through the tendon portion 3 and through the needle holes 334 to a hard stop. At the hard stop, the needles 300 are positioned within the tendon portion 3 and within the needle holes 334 so that the pointed end 306 of each of the needles 300 may be positioned within a corresponding one of the tip openings 340 defined in the needle tip guard 330. The needle tip guard 330 may cause the hard stop in downward movement of the needles 300.

Figure 31B:
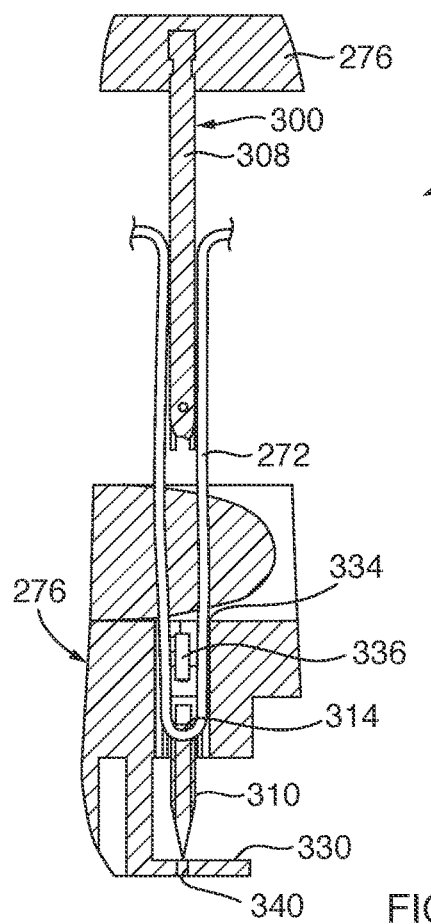
FIG. 31B is a cross-sectional view of a portion of the passer device system taken from section line B-B of FIG. 31, according to another embodiment of the present invention.

With respect to FIGS. 30, 31 and 31B, upon the needles 300 being moved downward to the hard stop, the pointed end 306 (FIG. 29) of a pointed end portion of the tip portion 310 of each of the needles 300 may engage the tip openings 340 with an interference type fit. At this stage, the knob 284 may be rotated back to move the needle base 276 away from the threading base 278, as shown by upward arrow 296. With this movement, the base portion 308 of the needles 300 may move with the needle base 276 such that the base portion 308 of the needles 300 moves out of the needle holes 334 and away from the tendon portion 3. Further, as the base portion 308 of the needles 300 moves with the needle base 276, the tip portion 310 of the needles 300 may be retained to the tip guard 330 such that the interference type fit holds the tip portion 310 in the tip openings 340 of the tip guard 330. As such, the interference type fit holding the tip portion 310 may be greater than the interconnection between the base portion 308 and the tip portion 310 of the needles 300. In another embodiment, other structure adjacent the tip openings 340 may be employed to hold the tip portion 310 of the needles 300 to the tip guard 330. The interconnection between the base portion 308 and the tip portion 310 of the needles 300 may be a snap type connection or interference type connection, or any other suitable separatable coupling. In this manner, the base portion 308 of the needles 300 may break-away from the tip portion 310 of the needles 300. Further, upon the base portion 308 of the needles 300 moving upward with the needle base 276, the loop 314 of the first suture 272 remains positioned adjacent one end of the tip portion 310 of the needles 300 such that the loop 314 associated with each one of the needles 300 may be positioned in the notch 312 (FIG. 28B) below the tendon portion and adjacent the suture guide slot 336.

Now with reference to FIGS. 31, 31A, 31B, and 32, the second suture 274 may be moved through the suture guide slot 336 and through each loop 314 associated with each tip portion 310 of the needles 300. Such movement of the second suture 274 may be employed with movement of the threader 350. As previously set forth, one end of the second suture 274 may be coupled to the threader 350. As such, the threader 350 may be driven through the threader guide channel 338 via rotation of a threader knob 360, as shown by rotational arrow 354, to rotate the gear 352. As the gear 352 rotates, gear teeth 358 may engage the aligned threader openings 356 defined in the threader 350 so that the threader 350 may be driven forward through the threader guide channel 338 and through the suture guide slot 336. Since one end of the second suture 274 is coupled to the threader 350, the second suture 274 also may be driven through the suture guide slot 336. With this arrangement, as the second suture 274 moves through the suture guide slot 336, the second suture 274 also is threaded through each of the openings defined by the loops 314 so that the second suture 274 becomes positioned in each of the loops 314 of the first suture 272.

Figure 32:
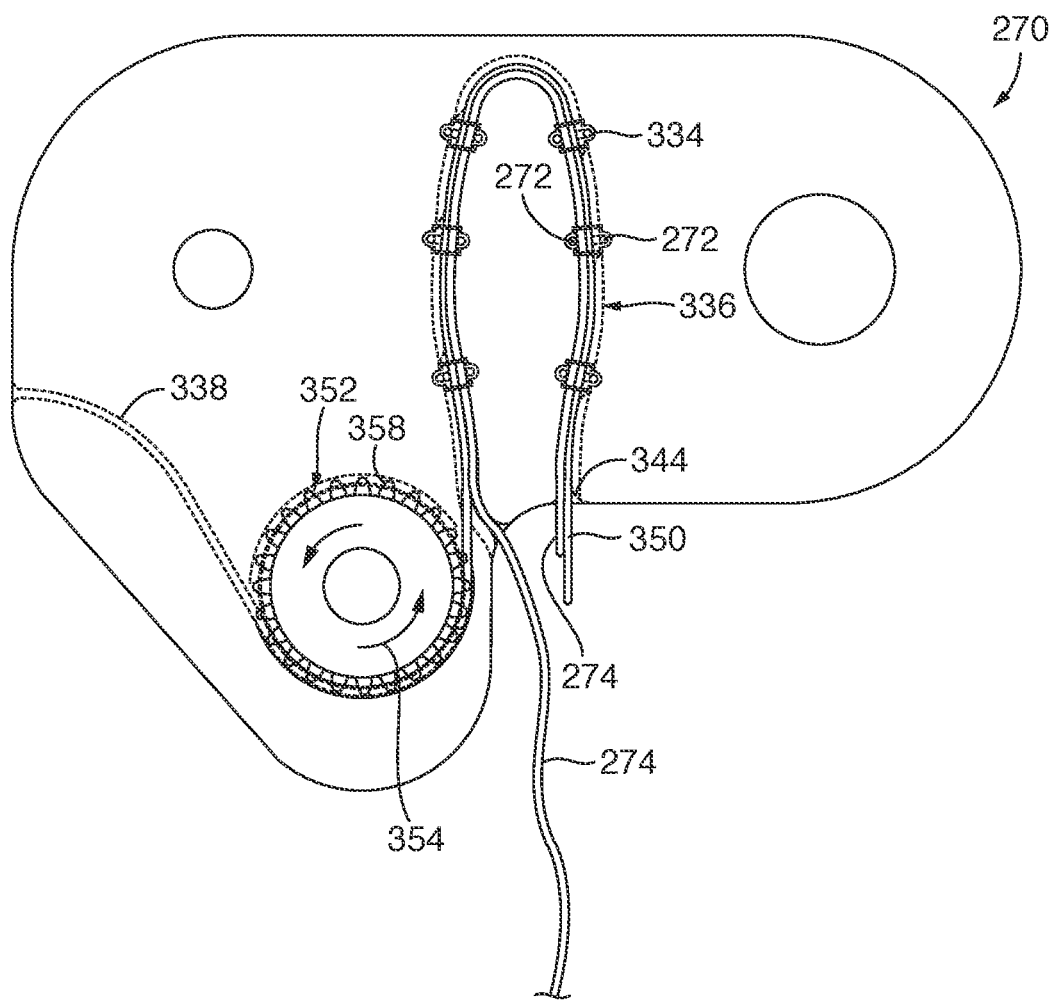
FIG. 32 is a cross-sectional view of the passer device system, depicting the threader and the threading suture both positioned in the suture guide slot in a second position, according to another embodiment of the present invention.
Figure 33:
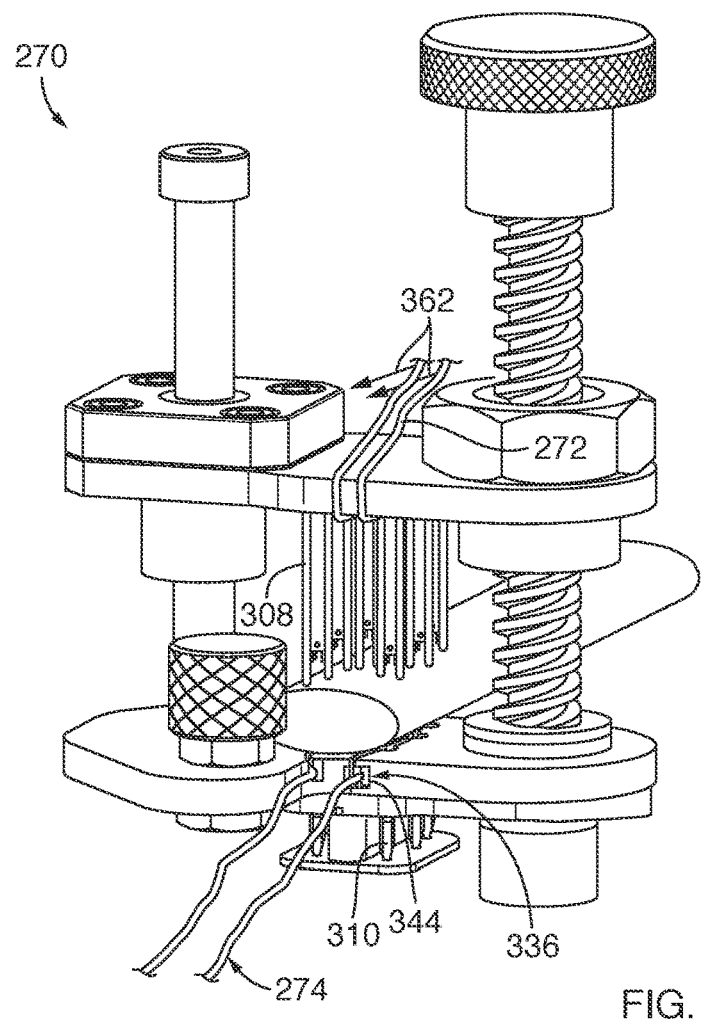
FIG. 33 is a perspective view of the passer device system, depicting the threading suture extending from both the entrance and exit openings of the suture guide slot, according to another embodiment of the present invention.
Figure 34:
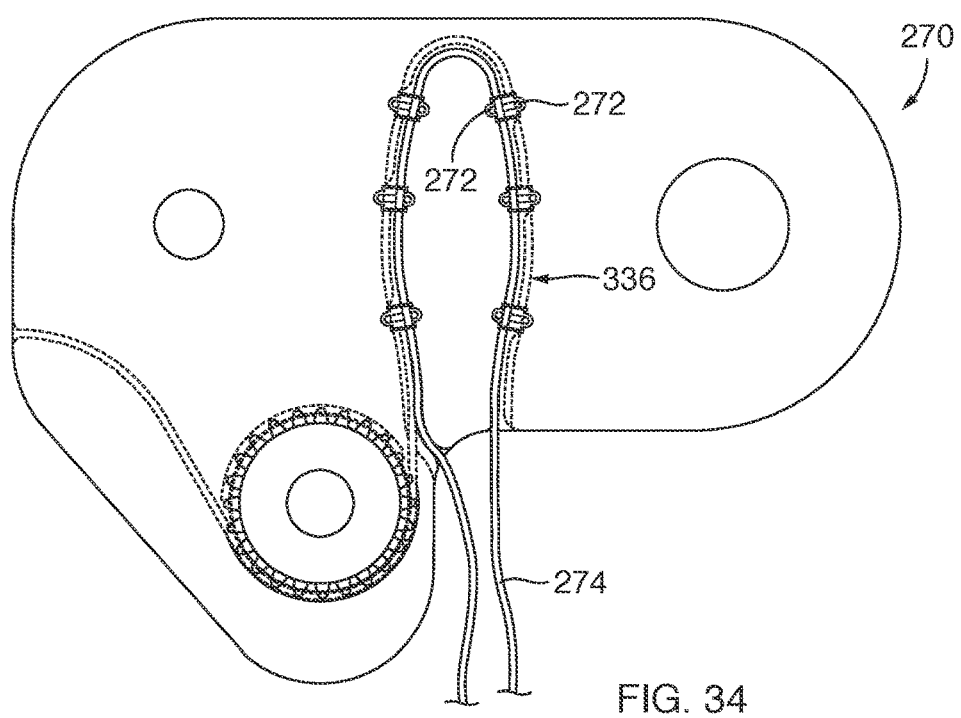
FIG. 34 is a cross-sectional view of the passer device system, depicting only the threading suture extending through the loop suture within the suture guide slot, according to another embodiment of the present.

As depicted in FIGS. 32 and 33, one end of the threader 350 may be exposed from the exit opening 344 of the guide slot 336. That one end of the threader 350 may then be manually pulled from the exit guide slot opening until the threader 350 is fully pulled from the suture guide slot 336. The threader 350 may then be manually removed from the second suture 274 such that the second suture remains in the suture guide slot 336, as depicted in FIGS. 33 and 34.

Figure 35:
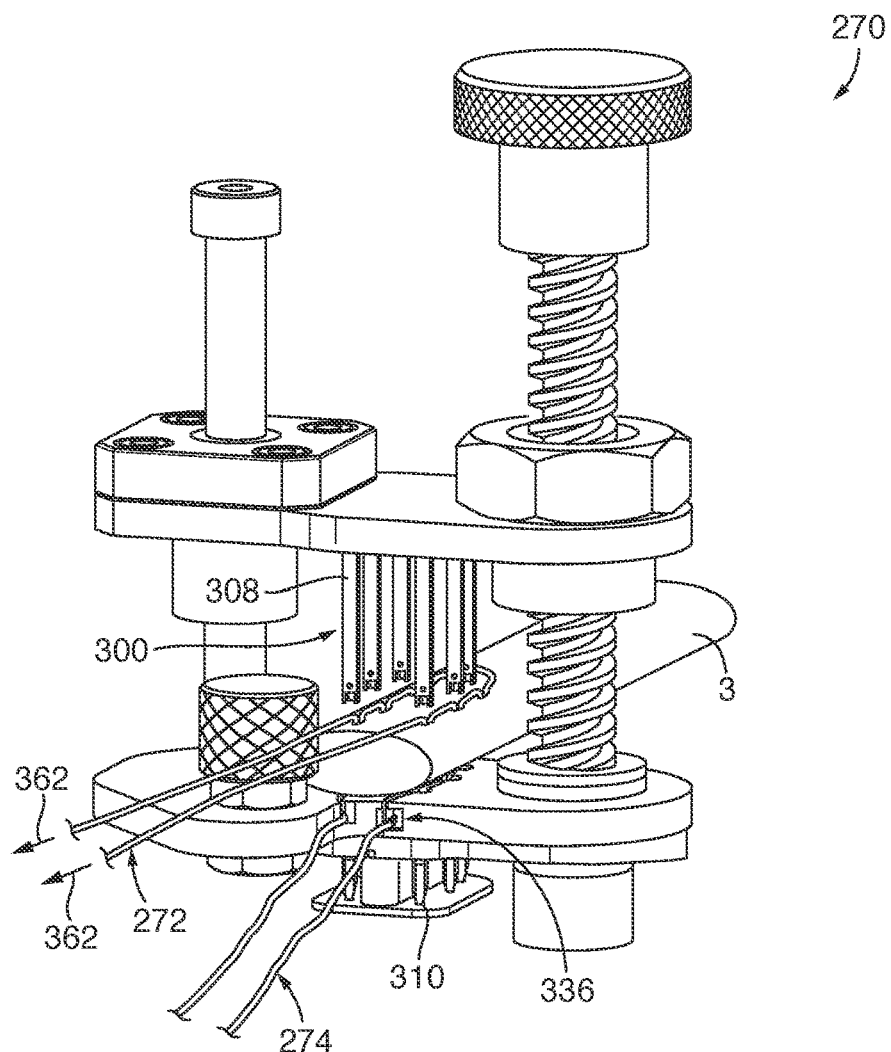
FIG. 35 is a perspective view of the passer device system, depicting the loop suture pulled away from the base portions of the needles, according to another embodiment of the present invention.
Figure 36:
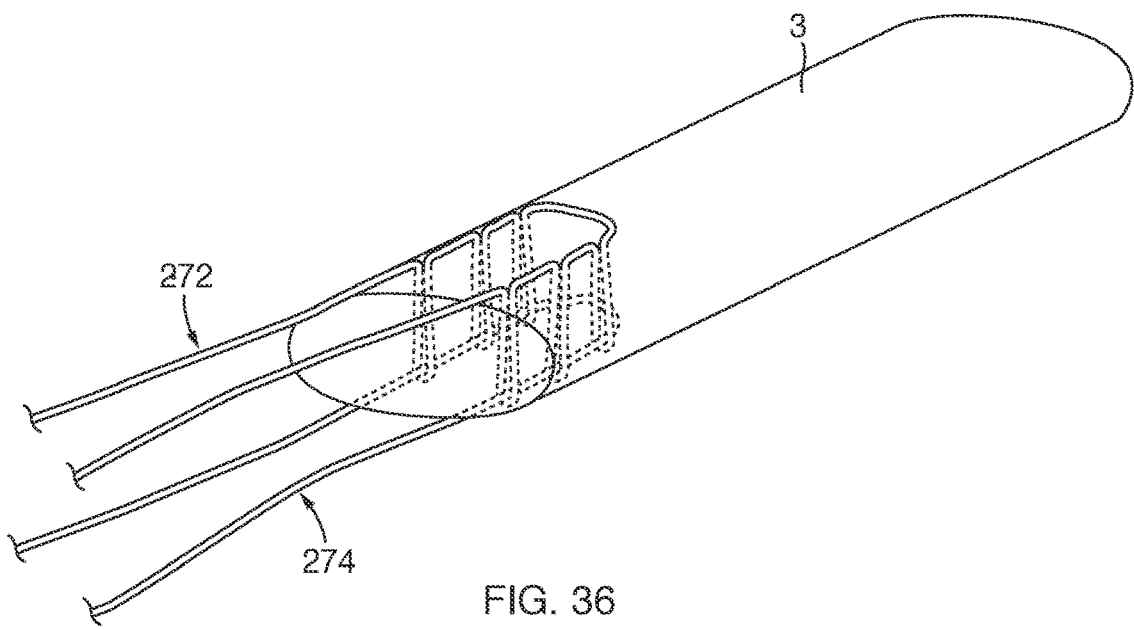
FIG. 36 is a perspective view of the loop suture and the threading suture coupled to the soft tissue portion, according to another embodiment of the present invention.

Now with reference to FIGS. 33-36, once the threader 350 (FIG. 32) has been removed from the second suture 274 (or the threader 350 has been removed from the suture guide slot 336), the first suture 272 may then be pulled from the base portion 308 of the needles 300. For example, first and second end portions or first and second portions of the first suture 272 may be pulled away from the needles 350, as shown by arrow 362, such that the first suture 272 may be released from being attached to the base portion 308 and from the neck of 315 (FIG. 28B) of the tip portion 310 of the needles 300, as shown in FIG. 35. Once the first suture 272 is completely pulled from the needles 350, the first and second sutures 272, 274 and the tendon portion 3 may be removed from the passer device 270, as depicted in FIG. 36. At this stage, the first suture 272 may be pulled taut to the extent of pulling any slack associated with the first suture 272, such as in the loops 314 (FIG. 31B), so that the loops 314 of the first suture 272 pull taut against the second suture 274 (some of first and second sutures 272, 274 shown in outline form). In this manner, the first and second sutures 272, 274 may be coupled to the tendon portion 3 in a similar arrangement as depicted in previous embodiments herein. Further, the end portions of the first and second sutures 272, 274 may then be coupled to, for example, a bone anchor 90 (FIG. 9), or to the end portions of first and second sutures coupled to a second tendon portion, as discussed in previous embodiments herein.

Figure 37:
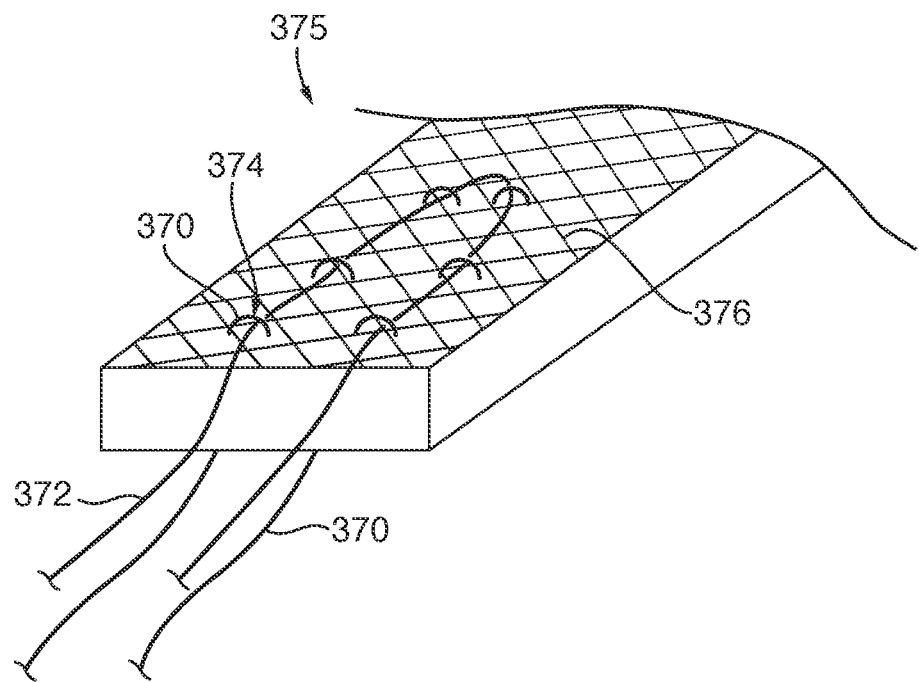
FIG. 37 is a perspective view of the loop suture and the threading suture coupled to the soft tissue portion, depicting one side of the soft tissue having a mesh material, according to another embodiment of the present invention.

Now with reference to FIG. 37, another embodiment that may be employed with any one of the embodiments of passer device systems herein is provided. In this embodiment, first and second sutures 370, 372 may be fixated to soft tissue, such as a tendon portion 3, with the passer device system 270 described and depicted in FIGS. 28-35, for example. The loops 374 of the first suture 370 depicted on one side 375 of the tendon portion 3 in FIG. 37 is the opposite side of the tendon portion depicted of the first and second sutures 272, 274 fixated to the tendon portion in FIG. 36. In this embodiment, the first and second sutures 370, 372 may be fixated to the tendon portion with a mesh portion 376 positioned along the one side 375 of the tendon portion 3. As such, the first and second sutures 370, 372 may assist in coupling the mesh portion 376 to the one side 375 of the tendon portion 3. Such may be implemented by positioning the mesh portion 376 on the first surface 320 of the threading base 278 (see FIG. 28) prior to positioning the tendon portion 3 over the first surface 320 of the threading base 278 (see FIG. 29). In another embodiment, the mesh portion 376 may be tacked onto the one side 375 of the tendon portion 3 prior to placing the tendon portion 3 over the first surface 320 of the threading base 278. Such mesh portion 376 may provide additional reinforcement to the interconnection of the first and second sutures 370, 372 to the tendon portion 3. The mesh portion 376 may be formed from a polymeric material, such as nylon, or any other material suitable as a reinforcement layer.

Figure 38:
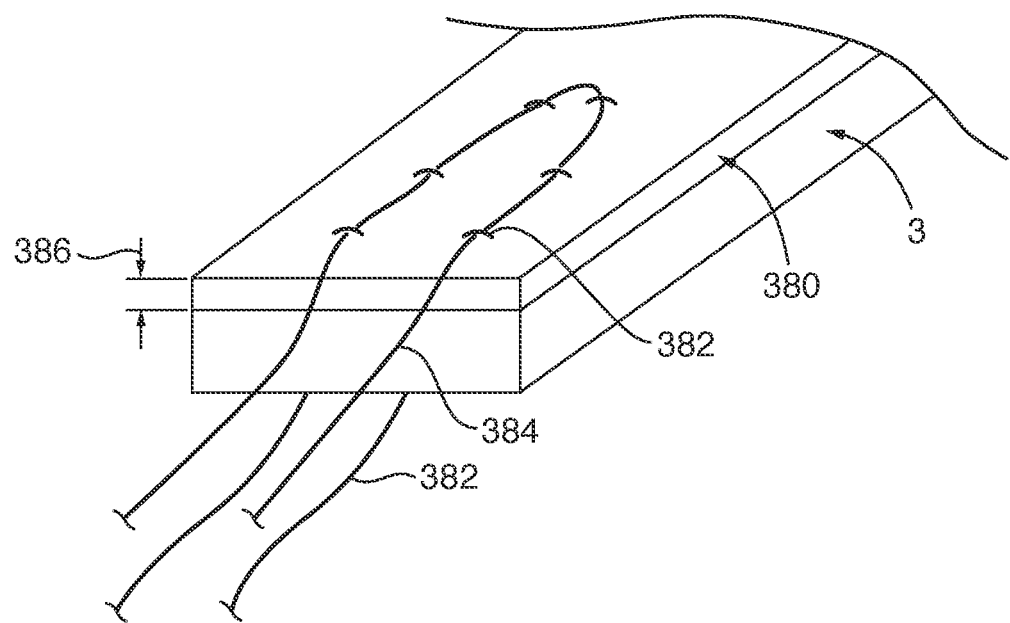
FIG. 38 is a perspective view of the loop suture and the threading suture coupled to the soft tissue portion, depicting one side of the soft tissue coupled with a reinforcement member, according to another embodiment of the present invention.

With reference to FIG. 38, another embodiment that may be employed with any one of the embodiments of passer device systems herein is provided. In this embodiment, similar to the previous embodiment, a reinforcement member 380 may be integrated with a tendon portion 3 that may be employed with the fixating of first and second sutures 382, 384 to the tendon portion 3, similar to that discussed in the previous embodiment. In this embodiment, the reinforcement member 380 may include a thickness 386 that may be similar to the thickness of the tendon portion 3, or thinner. Further, the reinforcement member 380 may be another soft tissue portion, such as another tendon portion, a ligament portion, or any other type of soft tissue. In another embodiment, the reinforcement member 380 may be a polymeric material or polymeric substrate. Such polymeric material may be a bioabsorbable material, as known in the art.

The first and second sutures referenced herein, in any one of the embodiments, may not be limited to typical medical grade suture material. Rather, any one of the first or second sutures set forth herein may be defined as a flexible filament. Such flexible filament may be any known flexible filament, of a natural fiber strand or polymeric strand that may not be typically employed as suture material. Further, the flexible filament may be a single strand or multiple strands woven together to effectively form a single strand. In another embodiment, the first and second sutures described herein may be flexible filaments of medical grade type sutures that may be typically employed for fixating to soft tissue.

The various components of the passer device systems described and depicted in the various embodiments herein may be formed using typical machining and molding techniques, or any other processes and techniques, as known to one of skill in the art. Further, each of the components associated with the passer device systems may be formed from metallic materials, such as stainless steel, titanium, aluminum or any other suitable metallic material, or any suitable medical grade polymeric materials, known in the art. Further, the threader may be formed from a Nitinol material, or a suitable polymeric material, as known to one of skill in the art.

The various passer device systems for coupling first and second sutures to soft tissue may be applied to any one of various soft tissue to soft tissue repairs as well as soft tissue to bone repairs. For example, the various passer device embodiments may be employed for flexor tendon repairs, patellar tendon repairs, Achilles tendon repairs, quadriceps tendon repairs, and/or bicep tendon repairs, or any other tendon, ligament, and tendon/ligament to bone repairs, such as kidner procedures or insertional Achilles repairs, or any other tendon/ligament to bone repairs. As such, the passer device systems set forth herein may be appropriately sized for proper fixation to the different sized or types of soft tissue.

While the invention may be susceptible to various modifications and alternative forms, specific embodiments have been shown by way of example in the drawings and have been described in detail herein. Further, the structural features of any one embodiment disclosed herein may be combined or replaced by any one of the structural features of another embodiment set forth herein. As such, it should be understood that the invention is not intended to be limited to the particular forms disclosed. Rather, the invention includes employing any portion of one embodiment with another embodiment, all modifications, equivalents, and alternatives, falling within the spirit and scope of the invention as defined by the following appended claims.

What is claimed is:

1. A passer device system for fixating soft tissue at a soft tissue repair site, the passer device system comprising:
   a passer base member;
   a threader base member coupled to the passer base member, the threader base member including a threader driver and a threader guide channel defined in the threader base member with a portion of the threader guide channel extending adjacent the threader driver, the threader base member defining passer holes and a suture guide slot therein;
   a threader configured to be moved through the threader guide channel and through the suture guide slot with movement of the threader driver;
   multiple passer devices extending from the passer base member and toward the threader base member such that each one of the passer devices corresponds with one of the passer holes defined in the threader base member, each of the passer devices extending with a length to a tip end and each of the passer devices defining a recess formed along the length thereof, each of the passer devices spaced from each other in a predetermined configuration;

a first suture sized and configured to extend along the recess of each of the passer devices such that, upon the multiple passer devices moving through the soft tissue, each of the passer devices moves the first suture through corresponding holes in tissue formed by the passer devices and into a corresponding one of the passer holes defined in the threader base member so that multiple loops are formed by the first suture along each corresponding passer device; and a second suture configured to be temporarily coupled to the threader, the second suture sized and configured to be threaded through the suture guide slot and configured to be driven by movement of the threader such that, upon the second suture being driven through the suture guide slot, the second suture extends through each of the loops and, upon the second suture being positioned within each of the loops, the passer devices are moveable from the soft tissue.

2. The passer device system of claim 1, wherein the recess may be a notch formed in the length of each one of the passer devices.

3. The passer device system of claim 1, wherein the recess extends with a hook structure, the hook structure sized and configured to temporally maintain the first suture in the recess.

4. The passer device system of claim 1, wherein the first suture extends with a continuous loop.

5. The passer device system of claim 1, wherein the first suture extends between first and second ends.

6. The passer device system of claim 1, wherein, upon the passer devices being withdrawn from the soft tissue, the first and second sutures are moveable to a taut position so as to be coupled to the soft tissue.

7. The passer device system of claim 1, wherein, upon the passer devices being withdrawn from the soft tissue, ends of at least one of the first and second sutures are couplable to a bone anchor.

8. The passer device system of claim 1, wherein the passer devices comprise a second recess defined along a length of each of the passer devices, the second recess configured to facilitate passing the second suture along the second recess.

9. The passer device system of claim 1, wherein each of the passer devices comprise a tip portion and a body, the tip portion being removably coupled to the body, the tip portion including arms that are moveable to an expanded position.

10. The passer device system of claim 1, wherein each of the passer devices comprise a tip portion and a body, the tip portion being removably coupled to the body such that, upon the passer devices being positioned within the passer holes and the second suture moves through each of the loops, the body and the tip portion of the passer devices separate.

11. The passer device system of claim 1, wherein the threader extends with multiple threader openings therein such that the threader is engageable with gears of the threader driver.

12. The passer device system of claim 1, wherein the suture guide slot defined in the threader base member intersects with the passer holes defined in the threader base member.

13. The passer device system of claim 1, wherein the passer holes defined in the threader base member each define a passer hole axis, the passer hole axis for each passer hole corresponds with a longitudinal axis of one of the passer devices, the suture guide slot defined in the threader base member extends to intersect each of the passer holes such that the suture guide slot extends substantially perpendicular relative to the passer hole axis for each of the passer holes.

14. The passer device system of claim 1, wherein the passer devices are coupled to the passer base member such that, upon the passer base member moving relative to the threader base member, each of the passer devices are moveable through the tissue and the passer holes in a simultaneous manner.

* * * * *